(12) United States Patent
Gatayama et al.

(10) Patent No.: US 10,531,843 B2
(45) Date of Patent: Jan. 14, 2020

(54) COUCH DEVICE, X-RAY CT APPARATUS, AND MEDICAL IMAGE DIAGNOSTIC APPARATUS

(71) Applicant: TOSHIBA MEDICAL SYSTEMS CORPORATION, Otawara-Shi (JP)

(72) Inventors: Kazuki Gatayama, Otawara (JP); Masao Yamahana, Nasushiobara (JP); Hiroyuki Onuki, Nasushiobara (JP); Shinya Kawanabe, Otawara (JP); Tatsuya Watanabe, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 768 days.

(21) Appl. No.: 14/945,970

(22) Filed: Nov. 19, 2015

(65) Prior Publication Data
US 2016/0151025 A1    Jun. 2, 2016

Related U.S. Application Data

(63) Continuation of application No. PCT/JP2014/064336, filed on May 29, 2014.

(30) Foreign Application Priority Data

May 29, 2013   (JP) ................................ 2013-112955

(51) Int. Cl.
  *A61B 6/03*     (2006.01)
  *A61B 6/04*     (2006.01)
(52) U.S. Cl.
  CPC ............ *A61B 6/0457* (2013.01); *A61B 6/032* (2013.01); *A61B 6/035* (2013.01); *A61B 6/04* (2013.01); *A61B 6/0407* (2013.01); *A61B 6/0442* (2013.01)

(58) Field of Classification Search
  CPC ........... A61B 6/032; A61B 6/035; A61B 6/04; A61B 6/0407; A61B 6/0442; A61B 6/0457
  (Continued)

(56) References Cited

U.S. PATENT DOCUMENTS 3,751,028 A * 8/1973 Scheininger ............. A61B 6/04
                                                  378/209
3,868,103 A * 2/1975 Pageot ................... A61G 13/02
                                                  137/596

(Continued)

FOREIGN PATENT DOCUMENTS

JP          1-308532         12/1989
JP          5-277097         10/1993
(Continued)

OTHER PUBLICATIONS

International Search Report dated Jun. 24, 2014 in PCT/JP2014/064336 filed May 29, 2014.
(Continued)

*Primary Examiner* — Allen C. Ho
(74) *Attorney, Agent, or Firm* — Oblon, McClelland, Maier & Neustadt, L.L.P.

(57) ABSTRACT

A couch device according to an embodiment includes a couchtop, shape control members, and driving circuitry. The couchtop includes a movable base couchtop and a transformable couchtop mounted above the movable base couchtop and capable of bending a part thereof from a flat shape. The shape control members control the shape of the transformable couchtop. The driving circuitry moves the couchtop to an opening of a gantry device that collects data for taking medical images. The transformable couchtop includes divided couchtops, and transformation support members for fixing the transformable couchtop to the movable base couchtop are fitted to divided sections. Each of the (Continued)

shape control members adjusts a position of a specific transformation support member so that an installation location thereof is a fixed point of the movable base couchtop.

17 Claims, 12 Drawing Sheets

(58) Field of Classification Search
USPC .................................. 378/20, 209; 5/601
See application file for complete search history.

(56) References Cited

U.S. PATENT DOCUMENTS

| | | | | |
|---|---|---|---|---|
| 5,349,956 A * | 9/1994 | Bonutti | A61B 5/0555 | |
| | | | | 5/601 |
| 5,386,446 A * | 1/1995 | Fujimoto | A61B 6/032 | |
| | | | | 378/15 |
| 5,740,222 A * | 4/1998 | Fujita | A61B 6/032 | |
| | | | | 378/4 |
| 6,295,671 B1 * | 10/2001 | Reesby | A61B 6/0442 | |
| | | | | 5/600 |
| 6,378,149 B1 * | 4/2002 | Sanders | A61B 6/0442 | |
| | | | | 378/209 |
| 6,843,182 B2 * | 1/2005 | Torcheboeuf | A61G 13/02 | |
| | | | | 108/143 |
| 6,862,762 B1 * | 3/2005 | Johnson | A61B 6/0442 | |
| | | | | 378/177 |
| 6,988,284 B2 * | 1/2006 | Bannister | A61B 6/0442 | |
| | | | | 378/209 |
| 7,151,816 B2 | 12/2006 | Maier et al. | | |
| 7,152,261 B2 * | 12/2006 | Jackson | A61G 7/001 | |
| | | | | 5/600 |
| 7,343,635 B2 * | 3/2008 | Jackson | A61G 7/001 | |
| | | | | 5/607 |
| 7,565,708 B2 * | 7/2009 | Jackson | A61G 7/001 | |
| | | | | 5/607 |
| 7,640,607 B2 * | 1/2010 | Guertin | A61B 5/064 | |
| | | | | 5/601 |
| 7,742,562 B2 * | 6/2010 | Weber | A61B 6/0457 | |
| | | | | 378/209 |
| 7,983,380 B2 * | 7/2011 | Guertin | A61B 5/064 | |
| | | | | 378/4 |
| 8,117,694 B2 * | 2/2012 | Farooqui | A61B 6/0457 | |
| | | | | 198/468.9 |
| 8,118,488 B2 * | 2/2012 | Gregerson | A61B 5/0555 | |
| | | | | 378/196 |
| 8,242,465 B2 * | 8/2012 | Iwata | G01N 23/00 | |
| | | | | 250/491.1 |
| 8,295,430 B2 * | 10/2012 | Zhu | A61N 5/10 | |
| | | | | 378/4 |
| 8,424,133 B1 * | 4/2013 | Rossi | A61B 6/0442 | |
| | | | | 5/601 |
| 8,536,547 B2 * | 9/2013 | Maurer, Jr. | A61N 5/1081 | |
| | | | | 250/492.3 |
| 8,578,529 B2 * | 11/2013 | Miyano | A61B 6/0457 | |
| | | | | 5/601 |
| 8,666,021 B2 * | 3/2014 | Fadler | A61B 6/032 | |
| | | | | 378/20 |
| 8,839,470 B2 * | 9/2014 | Ramos | A61B 6/0457 | |
| | | | | 5/601 |
| 8,888,364 B2 * | 11/2014 | Bailey | A61B 6/035 | |
| | | | | 378/198 |
| 8,904,582 B2 * | 12/2014 | Bergfjord | A61G 13/06 | |
| | | | | 378/209 |
| 8,953,862 B2 * | 2/2015 | Date | A61B 6/032 | |
| | | | | 382/131 |
| 9,061,141 B2 * | 6/2015 | Brunker | A61B 6/0442 | |
| 9,095,263 B2 * | 8/2015 | Krieg | A61B 6/487 | |
| 9,113,804 B2 * | 8/2015 | Kimishima | A61B 6/0407 | |
| 9,125,782 B2 * | 9/2015 | Hall | A61B 6/04 | |
| 9,144,409 B1 * | 9/2015 | Ocel | A61B 6/0442 | |
| 9,168,009 B2 * | 10/2015 | Lee | A61B 6/0428 | |
| 9,211,223 B2 * | 12/2015 | Jackson | A61G 7/001 | |
| 9,240,045 B2 * | 1/2016 | Noshi | A61B 6/0407 | |
| 9,259,170 B2 * | 2/2016 | Khamaisi | A61B 5/0555 | |
| 9,282,936 B2 * | 3/2016 | Kondo | A61B 6/032 | |
| 9,282,937 B2 * | 3/2016 | Shibata | A61B 6/0407 | |
| 9,326,907 B2 * | 5/2016 | Marie | A61G 7/1057 | |
| 9,433,388 B2 * | 9/2016 | Noshi | A61B 6/032 | |
| 9,462,981 B2 * | 10/2016 | Padwa | A61B 6/467 | |
| 9,498,167 B2 * | 11/2016 | Mostafavi | A61B 5/064 | |
| 9,504,437 B2 * | 11/2016 | Noshi | A61B 6/5235 | |
| 9,512,896 B2 * | 12/2016 | Grams | F16F 15/022 | |
| 9,549,706 B2 * | 1/2017 | Zhang | A61B 6/0407 | |
| 9,585,596 B2 * | 3/2017 | Bae | A61B 6/0407 | |
| 9,592,024 B2 * | 3/2017 | Iizuka | A61B 5/0555 | |
| 9,597,043 B1 * | 3/2017 | Mirza | A61B 6/0421 | |
| 9,610,049 B2 * | 4/2017 | Xu | G01R 33/28 | |
| 9,662,256 B2 * | 5/2017 | Marle | A61G 7/1057 | |
| 9,687,200 B2 * | 6/2017 | Maurer, Jr. | A61B 6/032 | |
| 9,693,740 B2 * | 7/2017 | Hori | A61B 6/0457 | |
| 9,700,265 B2 * | 7/2017 | Eder | A61B 6/0421 | |
| 9,750,468 B2 * | 9/2017 | Pettinato | A61B 6/0407 | |
| 9,757,075 B2 * | 9/2017 | Mukumoto | A61B 6/03 | |
| 9,782,315 B2 * | 10/2017 | Langford | A61G 13/10 | |
| 9,789,021 B2 * | 10/2017 | Sunazuka | A61G 13/10 | |
| 9,808,212 B2 * | 11/2017 | Kodaira | A61B 6/04 | |
| 9,833,208 B2 * | 12/2017 | Amano | A61B 6/4447 | |
| 9,848,798 B2 * | 12/2017 | Candidus | A61B 5/0555 | |
| 9,872,658 B2 * | 1/2018 | Yamada | A61B 6/032 | |
| 9,955,923 B2 * | 5/2018 | Batzer | A61B 5/6892 | |
| 9,962,132 B2 * | 5/2018 | Gregerson | A61B 6/4435 | |
| 2009/0300843 A1 | 12/2009 | Matsushita et al. | | |

FOREIGN PATENT DOCUMENTS

| | | |
|---|---|---|
| JP | 10-192269 | 7/1998 |
| JP | 2005-176955 | 7/2005 |
| JP | 2005-246057 | 9/2005 |
| JP | 2009-28160 | 2/2009 |
| JP | 2009-261440 | 11/2009 |
| JP | 2010-68858 | 4/2010 |
| JP | 2012-245209 | 12/2012 |
| WO | WO 2007/007583 A1 | 1/2007 |

OTHER PUBLICATIONS

Written Opinion dated Jun. 24, 2014 in PCT/JP2014/064336 filed May 29, 2014.

* cited by examiner

| IMAGING PLAN | SHAPE |
|---|---|
| SWALLOWING MOVEMENTS | SITTING POSITION |
| INSPIRATION AND EXPIRATION MOVEMENTS | SITTING POSITION |
| VOLUME | SITTING POSITION |
| . | . |
| . | . |
| . | . |

US 10,531,843 B2

COUCH DEVICE, X-RAY CT APPARATUS, AND MEDICAL IMAGE DIAGNOSTIC APPARATUS

CROSS-REFERENCE TO RELATED APPLICATIONS

This application is a continuation of PCT international application Ser. No. PCT/JP2014/064336 filed on May 29, 2014 which designates the United States, incorporated herein by reference, and which claims the benefit of priority from Japanese Patent Applications No. 2013-112955, filed on May 29, 2013, incorporated herein by reference.

FIELD

Embodiments described herein relate generally to a couch device, an X-ray CT apparatus, and a medical image diagnostic apparatus.

BACKGROUND

Medical image diagnostic apparatuses such as an X-ray computed tomography (CT) apparatus and a magnetic resonance imaging (MRI) apparatus include a couch device for moving a subject towards an opening of a gantry device for taking medical images. In conventional couch devices, a couchtop on which a subject is to be laid is in a flat shape. The conventional couch devices also include a moving mechanism for moving the couchtop in the forward and backward direction (longitudinal direction), and in the vertical direction. A couch device that includes a moving mechanism for moving the couchtop to the left and right (short side direction) is also known.

During a clinical examination, a patient is laid on a couchtop, the couchtop is moved in the forward and backward direction (or to the left and right), to take an image of a target portion. When a patient is laid on the couchtop before imaging takes place, the couch device moves the couchtop in the vertical direction to change the height of the couchtop, so that the patient can move smoothly onto the couchtop.

However, even if the height of the couchtop is changed to reduce the patient's burden of moving, when imaging is performed on an elderly and the like, the burdens on the patient, caregivers, or examination staffs, may remain heavy. Because it takes time to move the couch, the examination time may be increased, and the examination efficiency may be deteriorated.

DETAILED DESCRIPTION

A couch device according to an embodiment includes a couchtop, shape control members, and driving circuitry. The couchtop includes a movable base couchtop and a transformable couchtop mounted above the movable base couchtop and capable of bending a part thereof from a flat shape. The shape control members control the shape of the transformable couchtop. The driving circuitry moves the couchtop to an opening of a gantry device that collects data for taking medical images. The transformable couchtop includes divided couchtops, and transformation support members for fixing the transformable couchtop to the movable base couchtop are fitted to divided sections. Each of the shape control members adjusts a position of a specific transformation support member no that an installation location thereof is a fixed point of the movable base couchtop.

Embodiments of a couch device wilt now be described in detail below with reference to the accompanying drawings. In the following embodiments, an X-ray CT apparatus provided with a couch device will be described.

First Embodiment

Figure 1:
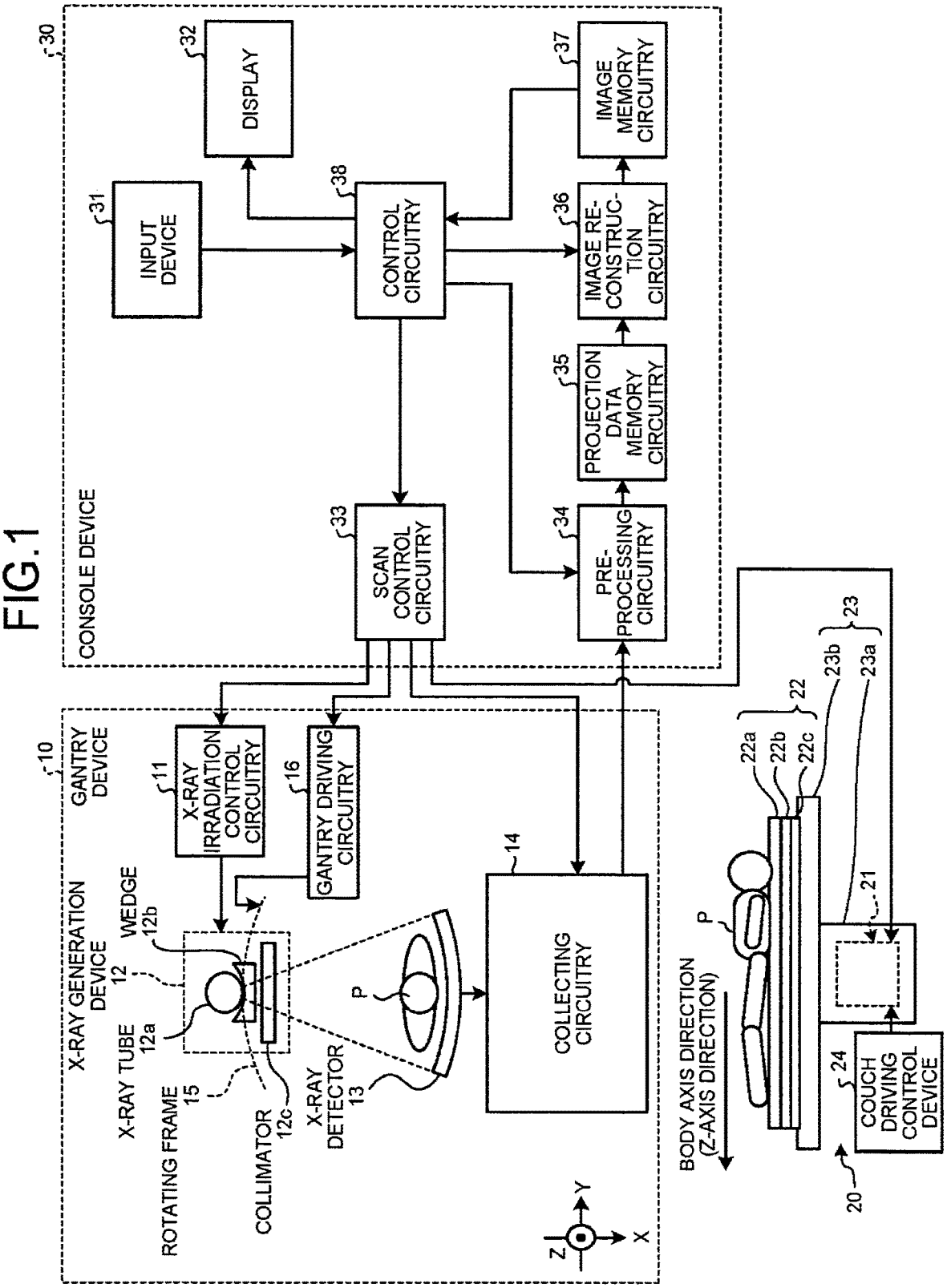
FIG. 1 is a configuration example of an X-ray CT apparatus according to a first embodiment.

A configuration of an X-ray CT apparatus according to a first embodiment will now be described. FIG. 1 is a configuration example of the X-ray CT apparatus according to the first embodiment. As illustrated in FIG. 1, the X-ray CT apparatus according to the first embodiment includes a gantry device 10, a couch device 20, and a console device 30.

The gantry device 10 is a device that has an opening into which a subject P is to be inserted, and collects data on detected X-rays. More specifically, the gantry device 10 is a device that irradiates the subject P inserted into the opening with X-rays, and collects data on detected X-rays that have passed through the subject P. As illustrated in FIG. 1, the gantry device 10 includes X-ray irradiation control circuitry 11, an X-ray generation device 12, an X-ray detector 13, collecting circuitry 14, a rotating frame 15, and gantry driving circuitry 16.

The rotating frame 15 supports the X-ray generation device 12 and the X-ray detector 13 facing each other interposing the subject P therebetween. The rotating frame 15 is an annular frame that rotates in a circular orbit around the subject P at a high speed by the gantry driving circuitry 16, which will be described in detail below.

The X-ray generation device 12 is a device that generates X-rays and irradiates the subject P with the generated X-rays. The X-ray generation device 12 includes an X-ray tube 12a, a wedge 12b, and a collimator 12c.

The X-ray tube 12a is a vacuum tube that generates X-ray beams with high voltage supplied from the X-ray irradiation control circuitry 11, which will be described in detail below. With the rotation of the rotating frame 15, the X-ray tube 12a exposes the subject P to X-ray beams. The X-ray tube 12a generates X-ray beams that spread over a fan angle and a cone angle.

The wedge 12b is an X-ray filter that adjusts the amount of X-rays exposed from the X-ray tube 12a. The collimator 12c is a slit that narrows down the irradiation range of the X-rays whose amount is adjusted by the wedge 12b, by the control of the X-ray irradiation control circuitry 11, which will be described in detail below.

The X-ray irradiation control circuitry 11 is a device that supplies high voltage to the X-ray tube 12a, as a high voltage generation circuitry. The X-ray tube 12a generates X-rays by using the high voltage supplied from the X-ray irradiation control circuitry 11. The X-ray irradiation control circuitry 11 adjusts the amount of X-rays emitted to the subject P, by adjusting the tube voltage and tube current supplied to the X-ray tube 12a. The X-ray irradiation control circuitry 11 also adjusts the irradiation range (fan angle and cone angle) of X-rays, by adjusting the degree of aperture of the collimator 12c.

The gantry driving circuitry 16 rotates the X-ray generation device 12 and the X-ray detector 13 in a circular orbit around the subject P, by rotating and driving the rotating frame 15.

The X-ray detector 13 detects the X-rays exposed from the X-ray tube 12a and that have passed through the subject P. For example, the X-ray detector 13 is a two-dimensional array type detector (plane detector) that detects X-ray intensity distribution data indicating the intensity distribution of X-rays emitted from the X-ray generation device 12 and that have passed through the subject P. A plurality of X-ray detection elements (detection element rows) arranged in the channel direction (Y-axis direction in FIG. 1), arc arranged on the X-ray detector 13 in a plurality of rows along the body axis direction (Z-axis direction in FIG. 1) of the subject P.

The collecting circuitry 14 is a data acquisition system (DAS), and generates X-ray detection data by performing amplification processing, analog-to-digital (A/D) conversion processing, and the like on the X-ray intensity distribution data detected by the X-ray detector 13. The collecting circuitry 14 then transmits the generated X-ray detection data to the console device 30, which will be described in detail below.

The couch device 20 is a device on Which the subject P is to be laid, and includes a couchtop 22 and a couch driving device 21. The couchtop 22 is a plate on which the subject P is to be laid. The couch driving device 21 moves the subject P into the rotating frame 15 (inside the opening), by moving the couchtop 22 in the Z-axis direction, under the control of scan control circuitry 33, which will be described in detail below.

In an examination using the X-ray CT apparatus, in general, a scanogram is taken. The scanogram is obtained by scanning the entire body of the subject P along the body axis direction, by moving the couchtop 22 while fixing the rotating frame 15 and emitting X-rays from the X-ray tube 12a. An operator who refers to the scanogram of the subject P, drafts an imaging plan. The scanogram is a positioning image for drafting an imaging plan of the subject P. Accordingly, for example, the gantry device 10 performs a helical scan in which the subject P is scanned in a spiral form, by moving the couchtop 22 and rotating the rotating frame 15. Alternatively, the gantry device 10 performs a conventional scan in which the subject P is scanned in a circular orbit by rotating the rotating frame 15, after moving the couchtop 22 and fixing the position of the subject P. Alternatively, the gantry device 10 performs a step-and-shoot method in which the position of the couchtop 22 is moved in a regular interval and a conventional scan is performed in a plurality of scanning areas.

The couch device 20 according to the first embodiment, as illustrated in FIG. 1, includes a support member 23 that supports the couchtop 22. The support member 23, as illustrated in FIG. 1, includes a support plate 23b in a flat shape that supports the couchtop 22, and a support leg 23a in a rectangular parallelepiped that supports the support plate 23b. The support plate 23b is fitted above the support leg 23a, which is installed on the floor surface. Accordingly, as illustrated in FIG. 1, the support member 23 is in a T-shape when viewed from the side. The couch driving device 21, which is driving circuitry provided in the couch device 20, is built inside the support leg 23a, as illustrated in FIG. 1. The X-ray CT apparatus according to the first embodiment also includes a couch driving control device 24 for controlling the couch driving device 21 near the couch device 20, as illustrated in FIG. 1, in addition to the scan control circuitry 33, which will be described in detail below. The operator can move the couchtop 22 by operating the couch driving control device 24, before or while imaging takes place.

The couchtop 22 of the couch device 20 according to the first embodiment, as illustrated in FIG. 1, includes a mattress 22a, a first couchtop 22b, and a second couchtop 22c. As illustrated in FIG. 1, the second couchtop 22c is arranged above the support plate 23b, the first couchtop 22b is arranged above the second couchtop 22c, and the mattress 22a is arranged above the first couchtop 22b. The mattress 22a, for example, is a cushion made of a flexible material such as sponge. The shape of the first couchtop 22b can be transformed so that the subject P can be laid thereon in any posture. The second couchtop 22c moves the first couchtop 22b to the opening of the gantry device 10. In other words, the second couchtop 22c is a "movable base couchtop" for moving the first couchtop 22b to the opening. For example, the second couchtop 22c is movable along a rail (not shown) installed in the support plate 23b, in the longitudinal direction. When the second couchtop 22c moves towards the opening in the longitudinal direction, the first couchtop 22b also moves towards the opening. The second couchtop 2c can also move in the short side direction, along a rail (not shown) installed in the support plate 23b. The support member 23 is formed to support the first couchtop 22b and the second couchtop 22c so as to be inclinable relative to the floor surface, More specifically, the support plate 23b is inclined relative to the floor surface, while being supported by the support leg 23a.

The couch driving device 21 according to the first embodiment transforms the first couchtop 22b and the second couchtop 22c, according to an instruction sent from the couch driving control device 24 or the scan control circuitry 33, which will be described in detail below. The couch driving device 21 according to the first embodiment inclines the support plate 23b, according to an instruction sent from the couch driving control device 24 or the scan control circuitry 33, which will be described in detail below. The operations of the couchtop 22 and the support member 23 performed in the first embodiment will be described in detail below.

The console device 30 is a device that receives the operation of the X-ray CT apparatus by the operator, and reconstructs X-ray CT image data from the X-ray detection data collected by the gantry device 10. The console device 30 includes an input device 31, a display 32, scan control circuitry 33, preprocessing circuitry 34, projection data memory circuitry 35, image reconstruction circuitry 36, image memory circuitry 37, and control circuitry 38.

The input device 31 includes a mouse, a keyboard, a button, afoot switch, or the like used to input various instructions and various settings by the operator of the X-ray CT apparatus. The input device 31 transmits instructions and the setting information received from the operator, to the control circuitry 38. For example, the operator inputs an instruction to move and control the couch device 20 by using the input device 31. Such an instruction is transmitted to the control circuitry 38, and the control circuitry 38 transmits the instruction received by the input device 31 to the scan control circuitry 33.

The display 32 is a monitor referred to by the operator. The display 32 displays X-ray CT image data for the operator and displays a graphical user interface (GUI) to receive various instructions, various settings, and the like, from the operator via the input device 31, under the control of the control circuitry 38.

The scan control circuitry 33 controls collection processing of X-ray detection data in the gantry device 10, by controlling the operations of the X-ray irradiation control circuitry 11, the gantry driving circuitry 16, the collecting circuitry 14, and the couch driving device 21, under the control of the control circuitry 38, which will be described in detail below.

The preprocessing circuitry 34 generates projection data by performing logarithmic conversion processing and correction processing such as an offset correction, a sensitivity correction, and a beam hardening correction, on the X-ray detection data generated by the collecting circuitry 14.

The projection data memory circuitry 35 stores therein projection data generated by the preprocessing circuitry 34. The image reconstruction circuitry 36 reconstructs the X-ray CT image data by using the projection data stored in the projection data memory circuitry 35. For example, the image reconstruction circuitry 36 reconstructs the X-ray CT image data of a plurality of axial planes, by using the projection data obtained by a helical scan, and generates volume data from the multiple pieces of X-ray CT image data. Alternatively, for example, the image reconstruction circuitry 36 reconstructs volume data corresponding to the X-ray CT image data of a plurality of axial planes, by using the projection data obtained by a conventional scan using the X-ray detector 13, which is a plane detector. There are various reconstruction methods, and for example, one of them is hack projection processing. For example, the back projection processing may be performed by a filtered back projection (FBP) method. Alternatively, the image reconstruction circuitry 36 may reconstruct the X-ray CT image data by using a successive approximation method.

The image reconstruction circuitry 36 can generate various pieces of image data, by performing various types of image processing on the X-ray CT image data. The image reconstruction circuitry 36 stores the reconstructed X-ray CT image data and the image data generated by various types of image processing, in the image memory circuitry 37. The image reconstruction circuitry 36 generates a scanogram from the projection data for generating scanogram stored in the projection data memory circuitry 35, and stores the generated scanogram in the image memory circuitry 37.

The control circuitry 38 controls the entire X-ray CT apparatus by controlling the operations of the gantry device 10, the couch device 20, and the console device 30. More specifically, the control circuitry 38 controls the CT scan performed in the gantry device 10, by controlling the scan control circuitry 33. The control circuitry 38 also controls the image reconstruction processing and the image generation processing at the console device 30, by controlling the preprocessing circuitry 34 and the image reconstruction circuitry 36. The control circuitry 38 also controls the display 32 to display various pieces of image data stored in the image memory circuitry 37 on the display 32.

The overall configuration of the X-ray CT apparatus according to the first embodiment has been described above. With this configuration, the X-ray CT apparatus according to the first embodiment performs imaging of the subject P laid on the couch device 20 described with reference to FIG. 1.

Figure 2:
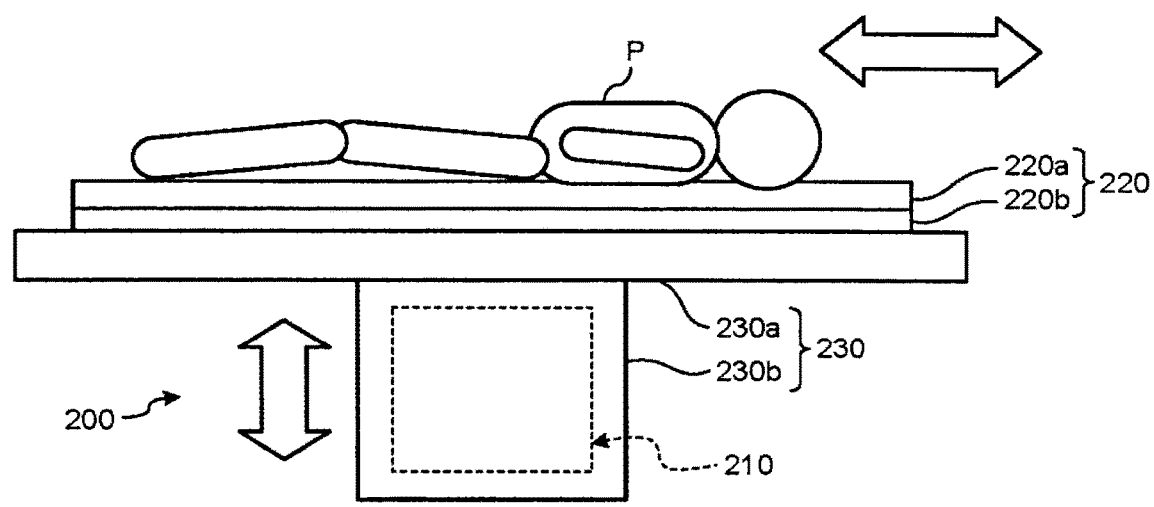
FIG. 2 is a schematic diagram for explaining an example of a conventional couch device.

Before describing the operation of the couch device 20 according to the first embodiment, a conventional couch device will be described with reference to FIG. 2. FIG. 2 is a schematic diagram for explaining an example of a conventional couch device.

A conventional couch device 200 illustrated in FIG. 2 includes a couchtop 220 on which the subject P is to be laid and a support member 230 that supports the couchtop 220. As illustrated in FIG. 2, the support member 230 includes a support plate 230*a* in a flat shape that supports the couchtop 220 and a support 230*b* in a rectangular parallelepiped that supports the support plate 230*a*. The support plate 230*a* is fitted above the support leg 230*b* that is installed on a floor surface. Accordingly, as illustrated in FIG. 2, the support member 230 is in a T-shape when viewed from the side. A conventional couch driving device 210 corresponding to the couch driving device 21, as illustrated in FIG. 2, is built inside the support leg 230*b*.

The couchtop 220 of the conventional couch device 200, as illustrated in FIG. 2, includes a mattress 220*a* and a movable couchtop 220*b*. As illustrated in FIG. 2, the movable couchtop 220*b* is arranged above the support plate 230*a*, and the mattress 220*a* is arranged above the movable couchtop 220*b*. The mattress 220*a*, for example, is a cushion made of a flexible material such as sponge. The movable couchtop 220*b* is in a flat shape. The movable couchtop 220*b* can move in the vertical direction, in the forward and backward direction (longitudinal direction), and to the left and right (short side direction), by the couch driving device 210.

During a clinical examination using the conventional couch device 200, after the subject P is laid on the couchtop 220, the couchtop 220 (movable couchtop 220*b*) is moved in the longitudinal direction. Alternatively, the couchtop 220 (movable couchtop 220*b*) is first moved in the short side direction and then moved in the longitudinal direction. Accordingly, the subject P is moved to the opening of the gantry device 10 to take X-ray CT image data. Conventionally, when the subject P is laid on the couchtop 220 before imaging takes place, the couch driving device 210 moved the couchtop 220 downward to the lower position, so that the subject P can be moved smoothly onto the couchtop 220.

However, even if the height of the couchtop 220 is changed to reduce the subject P's burden of moving, when imaging is performed on an elderly, the burdens on the subject P, caregivers, or examination staffs, may still remain heavy. In the conventional couch device 200, as described above, if it takes time to move the subject P onto the couchtop 220, the examination time may be increased, and the examination efficiency may be deteriorated.

Accordingly, in the first embodiment, to reduce the preparation time for imaging, the couch device 20 illustrated in FIG. 1 is installed in the X-ray CT apparatus. As described above, the couch device 20 according to the first embodiment includes the first couchtop 22*b* that can be transformed so that the subject P can be laid on in any posture, and the second couchtop 22c that moves the first couchtop 22b to the opening of the gantry device 10, as the couchtop 22. The first couchtop 22b is mounted above the second couchtop 22c, and is a "transformable couchtop" capable of bending a part thereof from a flat shape. As described above, the support member 23 provided in the couch device 20 according to the first embodiment supports the first couchtop 22b and the second couchtop 22c so as to be inclinable relative to the floor surface.

Figure 3:
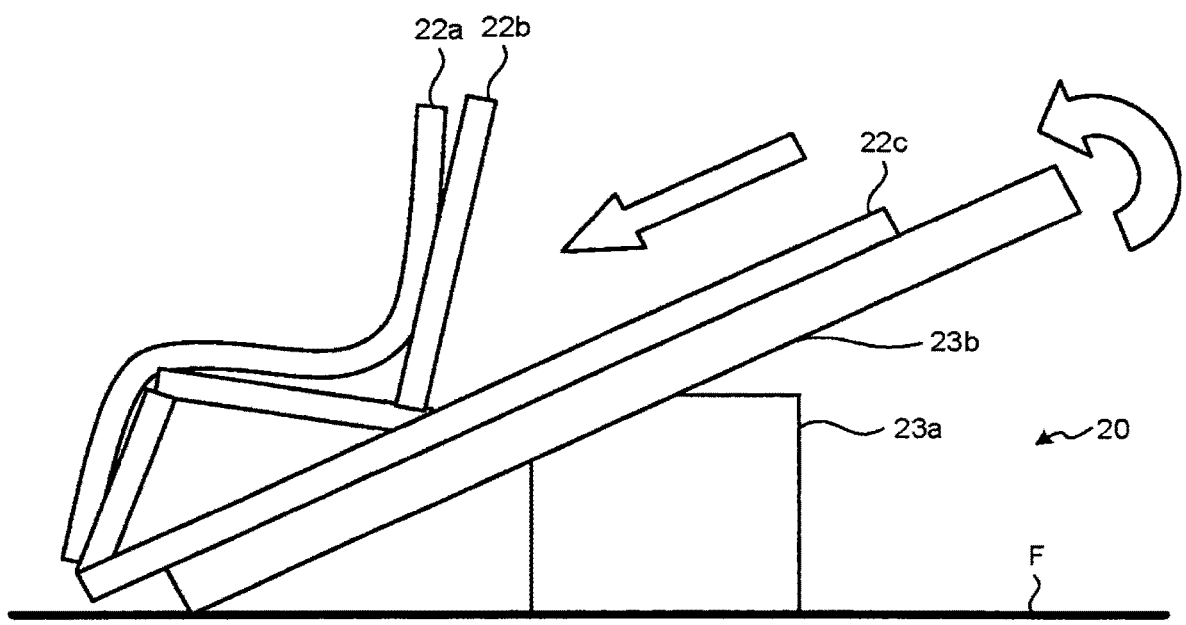
FIG. 3, FIG. 4, FIG. 5 and FIG. 6 are schematic diagrams of an operation example of a couch device according to the first embodiment.

FIGS. 3 to 6 are schematic diagrams illustrating operation examples of the couch device according to the first embodiment. The couch driving device 21 according to the first embodiment can move the couchtop 22 (support plate 23b) in the vertical direction before imaging takes place. The couch driving device 21 according to the first embodiment, as illustrated in FIG. 3, can further incline the support plate 23b around the support leg 23a, relative to a floor surface F. In the example illustrated in FIG. 3, the support plate 23b is inclined counterclockwise around the rotating shaft along the short side direction, to the position close to the location of the subject P, which is not shown, relative to the floor surface F.

Furthermore, the couch driving device 21 according to the first embodiment transforms the first couchtop 22b into the shape so that the subject P can easily move onto, as illustrated in FIG. 3, before imaging takes place. In the example illustrated in FIG. 3, the first couchtop 22b includes three parts arranged along the longitudinal direction. The first part is rotatably connected to the second part via a first rotating shaft along the short side direction. The second part is rotatably connected to the third part via a second rotating shaft along the short side direction. The first rotating shaft and the second rotating shaft each enable the three parts to rotate. By rotating the three parts, the first couchtop 22b can transform its shape. In the example illustrated in FIG. 3, the first couchtop 22b is transformed into the shape of a chair, so that the subject P can be moved while in a sitting position. In the example illustrated in FIG. 3, to bring the first couchtop 22b, which is transformed into the shape of a chair, closer to the floor surface F, the couch driving device 21 moves the second couchtop 22c downward along the support plate 23b.

Figure 4:
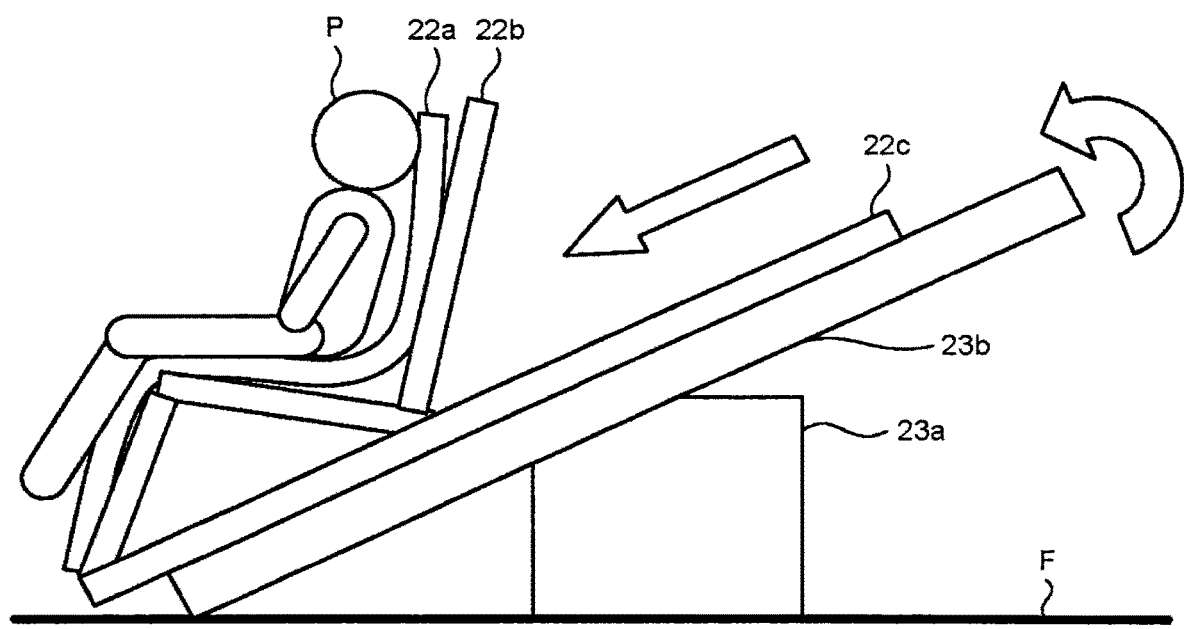

Accordingly, for example, the subject P who is moved to an examination room on a wheelchair, as illustrated in FIG. 4, can easily be moved onto the mattress 22a on the first couchtop 22b, which is brought to the position close to the floor surface F, while in a sitting position. With the transformation of the first couchtop 22b, the shape of the mattress 22a is also transformed into the shape of a chair. However, if the subject P can be moved smoothly onto the first couchtop 22b, which is transformed into the shape of a chair, while the support plate 23b is moved downward, there is no need to incline the support member 23.

Figure 5:
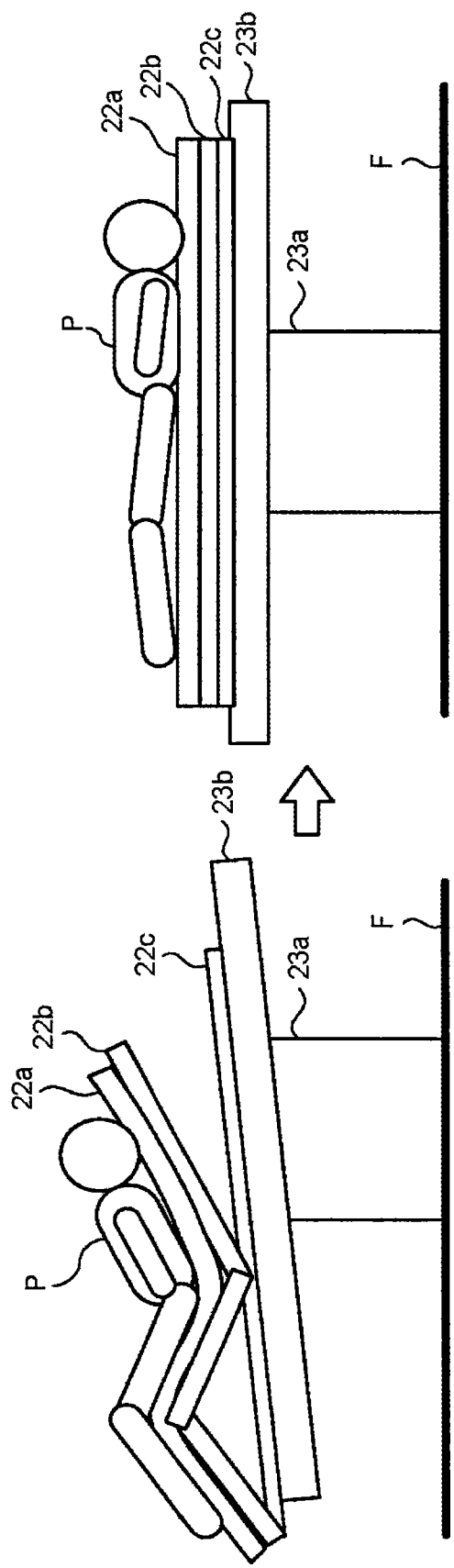

The first couchtop 22b, as illustrated in the left and right diagrams in FIG. 5, is transformed into a flat shape, while moving to the opening. When the support member 23 is inclined, as illustrated in the left and right diagrams in FIG. 5, the support member 23 is returned in the horizontal direction, while the first couchtop 22b is moved to the opening. In the example illustrated in FIG. 5, the posture of the subject P is changed from the sitting position to the face-up position, which is the posture taken for normal imaging. While the above-described operation is in progress, the couch driving device 21 controls the inclined support plate 23b to return to the horizontal state, before controlling the first couchtop 22b to return to the horizontal state, so that the subject P can smoothly shift to the face-up position.

Figure 6:
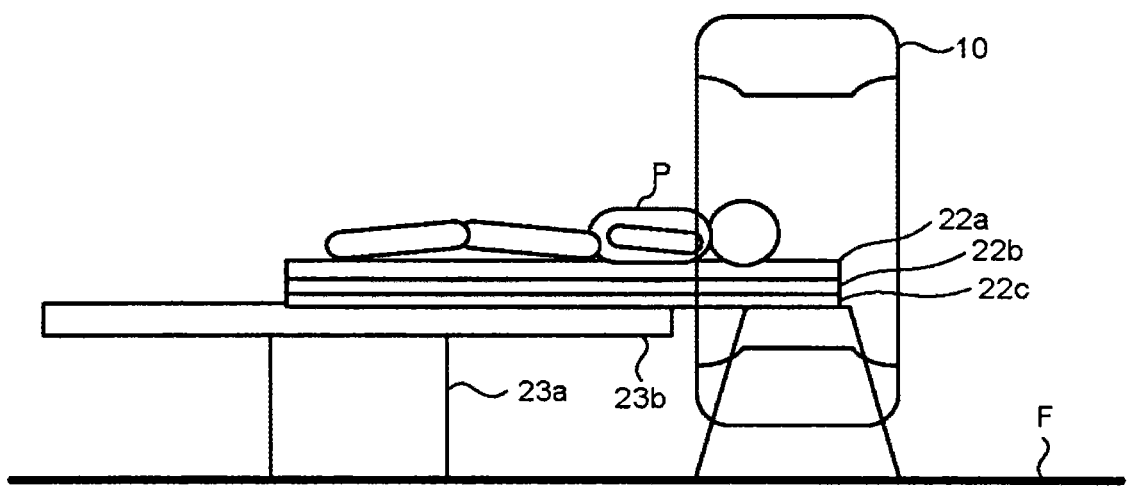

The couch driving device 21, for example, adjusts the height and the position in the short side direction of the couchtop 22, and moves the second couchtop 22c, by the control of the couch driving control device 24 that received an instruction from the operator. The subject P, as illustrated in FIG. 6, is then moved to the opening of the gantry device 10. The X-ray CT apparatus then performs imaging on the subject P.

When the imaging on the subject P is finished, the couch device 20 shifts from the state illustrated in FIG. 6 to the state illustrated in the right diagram in FIG. 5. The couch device 20 then shifts from the state illustrated in the right diagram in FIG. 5, to the state illustrated in the left diagram in FIG. 5, and further shifts to the state illustrated in FIG. 4. Consequently, the subject P can easily leave the couch device 20, While in the sitting position.

The operational controls described in FIGS. 3 to 5 are executed, for example, when the operator operates the couch driving control device 24. The operational control described in FIG. 6 is executed, for example, when the operator operates the console device 30.

As described above, in the first embodiment, the first couchtop 22b that can transform its shape is used as the couchtop 22. In the first embodiment, the support member 23 that supports the couchtop 22 is inclinable relative to the floor surface F. Thus, in the first embodiment, for example, the subject P can easily move onto the couch device 20, while in the sitting position, by inclining the support plate 23b close to the floor surface F, and transforming the first couchtop 22b into the shape of a chair. As a result, in the first embodiment, the preparation time for imaging can be reduced. Also, in the first embodiment, because the subject P can be easily moved onto the couch device 20, it is possible to reduce the burdens on the subject P, caregivers of the subject P, and examination staffs.

Figure 7:
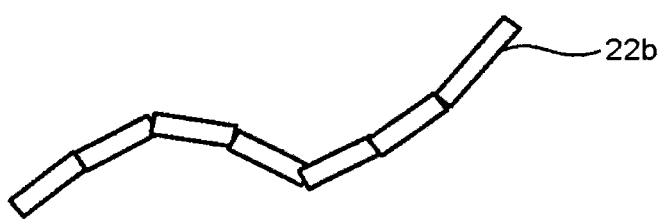
FIG. 7 and FIG. 8 are schematic diagrams of a modification of the couch device according to the first embodiment.
Figure 8:
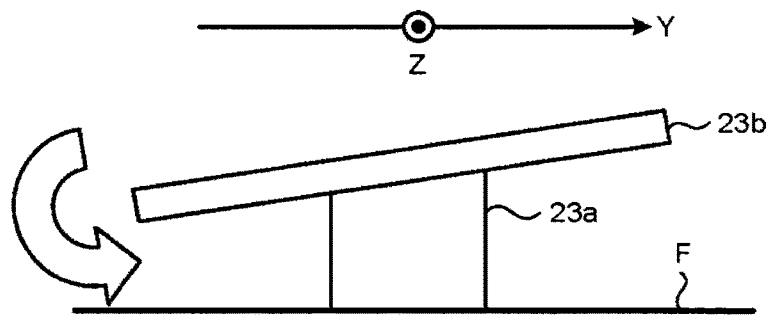

The configuration of the first couchtop 22b is not limited to that explained with reference to FIG. 3. The support member 23 (support plate 23b) may also perform inclination operations in addition to the inclination operation explained with reference to FIG. 3. These will be explained with reference to FIG. 7 and FIG. 8. FIGS. 7 and 8 are schematic diagrams of modifications of the couch device according to the first embodiment.

For example, the first couchtop 22b, as illustrated in FIG. 7, is made of seven parts arranged along the longitudinal direction. The seven parts of the first couchtop 22b are connected with rotating shafts along the short side direction. Accordingly, the first couchtop 22b illustrated in FIG. 7 can be transformed more freely than that illustrated in FIG. 3, due to the rotating shafts. By using the first couchtop 22b that can be transformed more freely, in the first embodiment, the mattress 22a can be transformed more flexibly along the body shape of the subject P. Also, for example, the first couchtop 22b may include a plurality of parts along each of the longitudinal direction and the short side direction. The first couchtop 22b configured in such a manner can be transformed so as to wrap the subject P.

For example, the support plate 23b, as illustrated in FIG. 8, may be formed so as to be inclinable with respect to the rotating shaft along the longitudinal direction. In the example illustrated in FIG. 8, the support plate 23b can be inclined with respect to the rotating shaft along the short side direction (rotating shaft in the Y direction), and also can be inclined with respect to the rotating shaft along the longitudinal direction (rotating shaft in the Z direction). By using the support plate 23b that can be inclined with respect to two rotating shafts, the subject P can be moved onto the couchtop 22 from any direction of the couch device 20.

Second Embodiment

Figure 9:
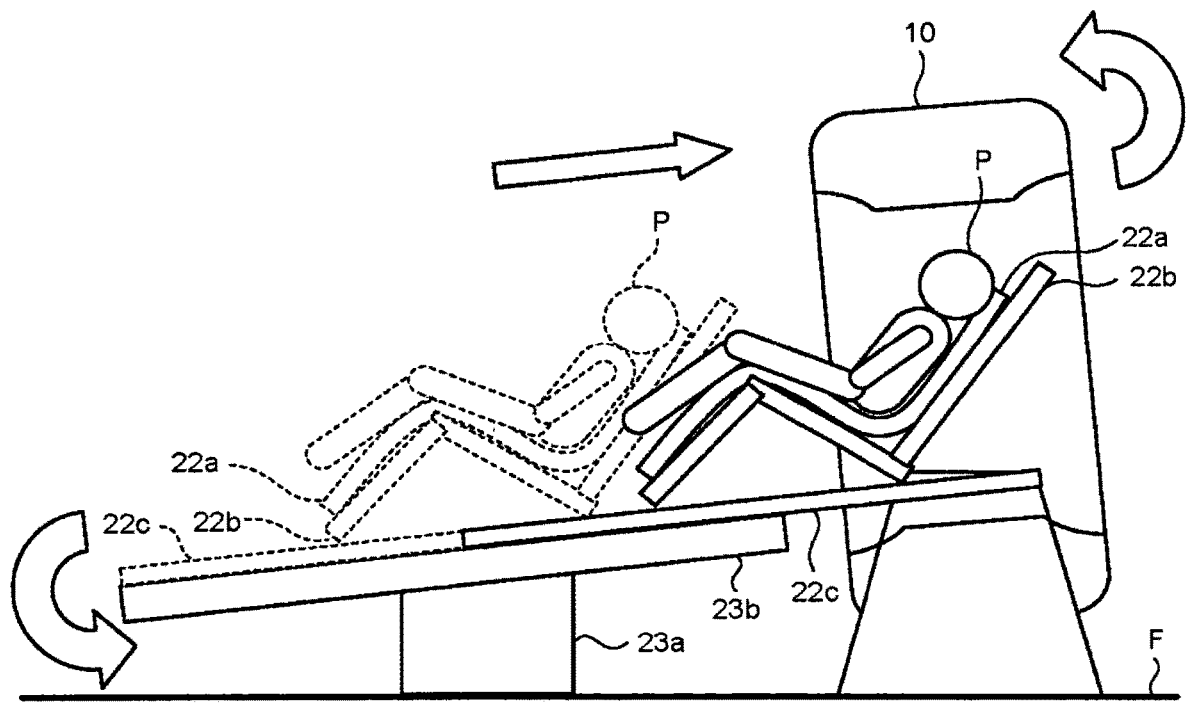
FIG. 9 is a schematic diagram of an operation example of a couch device and a gantry device according to a second embodiment.

In the first embodiment, the first couchtop 22b, which is a transformable couchtop, is returned to a flat shape at the time of imaging. In the second embodiment, a situation when the shape of the first couchtop 22b is transformed while imaging takes place, is described with reference to FIG. 9 and the like. FIG. 9 is a schematic diagram of an operation example of a couch device and a gantry device according to the second embodiment.

An X-ray CT apparatus according to the second embodiment is configured the same as the X-ray CT apparatus according to the first embodiment described with reference to FIG. 1. Depending on the health condition, there is a possibility that the subject P has difficulty in stretching himself or herself. In such a case, the burden on the subject P is reduced, when imaging takes place in the sitting position, which is the posture when the subject P is mounted on. The first couchtop 22b according to the second embodiment is moved to the opening, while keeping the transformed shape when the subject P is mounted thereon. The support member 23 according to the second embodiment is maintained in an inclined state when the subject P is mounted thereon, while the first couchtop 22b is moved to the opening.

Depending on the purpose of imaging, the face-up position may not be a posture suitable for imaging. In such a case, the first couchtop 22b is preferably transformed so that the posture of the subject P is suitable for imaging, and the support member 23 is inclined so that the subject P is in a posture suitable for imaging. In the second embodiment, not only imaging takes place while maintaining the first couchtop 22b and the support member 23 in a state when the subject P is mounted thereon, but the following operational control may also be performed. In other words, in the second embodiment, the first couchtop 22b is moved to the opening, while it is transformed into the shape so that the posture of the subject P is in a posture suitable for imaging. The support member 23 is also inclined so that the posture of the subject P is in a posture suitable for imaging. The above described "posture suitable for imaging" will be described in detail below.

However, depending on the size of the opening, the first couchtop 22b in the transformed state may come into contact with the gantry device 10, and may not be able to move into the opening. Accordingly, when the first couchtop 22b is moved to the opening while the shape thereof is being transformed, the gantry device 10 according to the second embodiment is inclined relative to the floor surface.

The above-described control, for example, is performed when the scan control circuitry 33 cooperatively controls the couch driving device 21 and the gantry driving circuitry 16. Alternatively, the above-described control, for example, is performed when the couch driving control device 24 cooperatively controls the couch driving device 21 and the gantry driving circuitry 16.

If the sitting position is not a burden on the subject P, or if the posture suitable for imaging is when the subject P is in the upright position, the first couchtop 22b transformed into the shape of a chair, as illustrated in FIG. 9, is moved towards the gantry device 10 in the longitudinal direction. More specifically, the first couchtop 22b is moved towards the gantry device 10 when the second couchtop 22c is moved towards the gantry device 10 along the longitudinal direction of the support plate 23b. The support plate 23b, as illustrated in FIG. 9, is inclined counterclockwise relative to the floor surface F.

The gantry driving circuitry 16, as illustrated in FIG. 9, then inclines the gantry device 10 relative to the floor surface F, so that the moving direction of the second couchtop 22c is perpendicular to the opening surface of the opening of the gantry device 10. More specifically, the gantry driving circuitry 16 inclines the gantry device 10 relative to the floor surface F, so that the moving direction of the second couchtop 22c and the rotating shaft of the rotating frame 15 are in parallel.

Accordingly, as illustrated in FIG. 9, the subject P can be moved inside the opening while in the sitting position, without coming into contact with the gantry device 10. When the imaging is finished, the second couchtop 22c is moved in the direction separated from the gantry device 10 along the longitudinal direction of the support plate 23b, while the gantry device 10 and the support plate 23b are still being inclined. The couch device 20, for example, is then moved to the state as illustrated in FIG. 4, so that the subject P can easily move away from the couch device 20. If the subject P sitting on the first couchtop 22b, which is transformed into the shape of a chair, can be moved into the opening without coming into contact with the opening, such as when the gantry device 10 is provided with a large opening and the like, there is no need to incline the gantry device 10.

As described above, in the second embodiment, for example, imaging can take place while the subject P is in the sitting position, by cooperatively inclining the gantry device 10 along with the transformation of the first couchtop 22b and the inclination of the support plate 23b. As a result, in the second embodiment, imaging can take place without imposing a burden on the subject P who has difficulty in stretching himself or herself. In the second embodiment, imaging can take place a plurality of times after finishing the first imaging, by making adjustments to change the portion to be imaged. The adjustments to change the portion to be imaged include readjustment of the transformation of the first couchtop 22b, readjustment of the position of the first couchtop 22b moved by the second couchtop 22c, readjustment of the inclination angle of the support member 23, and readjustment of the inclination angle of the gantry device 10.

Figure 10A:
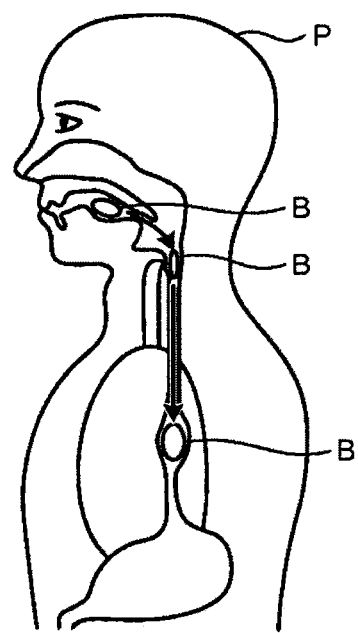
FIG. 10A, FIG. 10B and FIG. 10C are schematic diagrams for explaining an effect of the second embodiment.
Figure 10B:
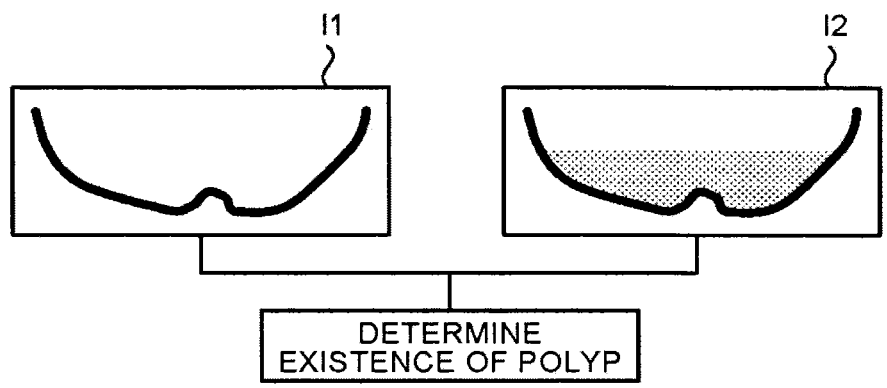
Figure 10C:
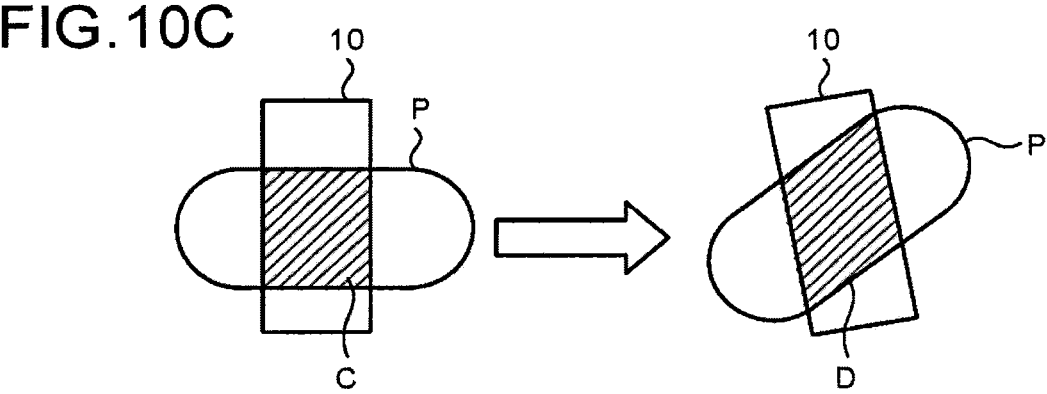

Moreover, by cooperatively inclining the gantry device 10 along with the transformation of the first couchtop 22b and the inclination of the support plate 23b, as illustrated in FIG. 10A, FIG. 10B, and FIG. 10C, the second embodiment can obtain various effects. FIG. 10A, FIG. 10B, and FIG. 10C are schematic diagrams for explaining the effects of the second embodiment.

Imaging usually takes place in a lying position, and due to this position, variations of dynamic imaging are limited. However, as described above, by cooperatively inclining the gantry device 10 along with the transformation of the first couchtop 22b and the inclination of the support plate 23b, in the second embodiment, imaging becomes possible in various postures. For example, the second embodiment enables dynamic imaging of swallowing, which is difficult in a lying position. As illustrated in FIG. 10A, food B taken by the subject P is transported to the pharynx and swallowed into the pharynx by reflex (deglutition). After the food B is swallowed, it passes through the esophagus and is transferred to the stomach. The airways to the lungs and the esophagus to the stomach are separated at the bottom of the pharynx. In general, at the moment of swallowing, portions of the pharynx close the entry to the airways by reflex in conjunction with each other, so as to prevent the food B from entering the lungs from the airways. Dynamic imaging of such swallowing is preferably taken in the upright position rather than a lying position.

In the second embodiment, as illustrated in FIG. 9, imaging of the subject P can take place while the subject P is sitting in the upright position. In other words, as illustrated in FIG. 9, when the subject P is moved to the opening and takes the food B in the second embodiment, it is possible to perform the successive imaging of the movements of the pharynx, which is carried out by reflex, in the act of swallowing illustrated in FIG. 10A. In the second embodiment, because imaging can take place while the subject P is sitting in the upright position, not only the dynamic imaging of swallowing, but also the successive imaging of the movements of the lungs during inspiration and expiration can take place, while the subject P is sitting in the upright position, in other words, in a natural state.

In the second embodiment, imaging is possible while the subject P is sitting in the upright position, and thus it is possible, for example, to perform imaging to determine the existence of a polyp in the lower half of the stomach. For example, the X-ray CT apparatus takes an image of the stomach while the subject P is sitting in the upright position. Accordingly, the image reconstruction circuitry 36, as illustrated in FIG. 10B, reconstructs image data I1 of the stomach. The X-ray CT apparatus then takes an image of the stomach of the subject P, while the subject P, who is sitting in the upright position, drinks a contrast agent. Consequently, the image reconstruction circuitry 36 reconstructs image data I2 of the stomach, as illustrated in FIG. 10B.

The operator then compares between the image data I1 and the image data I2, and confirms the shape of the lower portion of the area enhanced by the contrast agent. As illustrated in FIG. 10B, the operator can determine the existence of a polyp. Alternatively, the image reconstruction circuitry 36 generates differential image data obtained by differentiating the image data I1 from the image data I2. The operator can determine the existence of a polyp, by observing the differential image data.

In the second embodiment, the gantry device 10 is cooperatively inclined along with the transformation of the first couchtop 22b and the inclination of the support plate 23b. Accordingly, as illustrated in FIG. 10C, imaging of the subject P can be performed on an imaging range D larger than an imaging range C, at which imaging is performed in a lying position. If the imaging range is increased, the reconstruction region is also increased. Consequently, the second embodiment enables an increase in the reconstruction region. Thus, for example, in the second embodiment, volume data of the imaging range D can be reconstructed by using a conventional scan in which the rotating frame 15 is rotated once, instead of a helical scan in which the rotating frame 15 is rotated a plurality of times. As a result, the second embodiment shortens the imaging time, and reduces the X-ray exposure dose. Also in the second embodiment, in which the reconstruction region can be increased, it is possible to reduce imaging time; thus, in the contrast imaging that observes the movement of the contrast agent over time, for example, it is possible to reduce the dose of contrast agent. The increase in the reconstruction region is also possible by only transforming the first couchtop 22b, or by only transforming the first couchtop 22b and inclining the support plate 23b.

The contents described in the first embodiment are also applicable in the second embodiment excluding the point that the transformed first couchtop 22b is moved to the inclined gantry device 10, while the support member 23 is being inclined.

Third Embodiment

Figure 11:
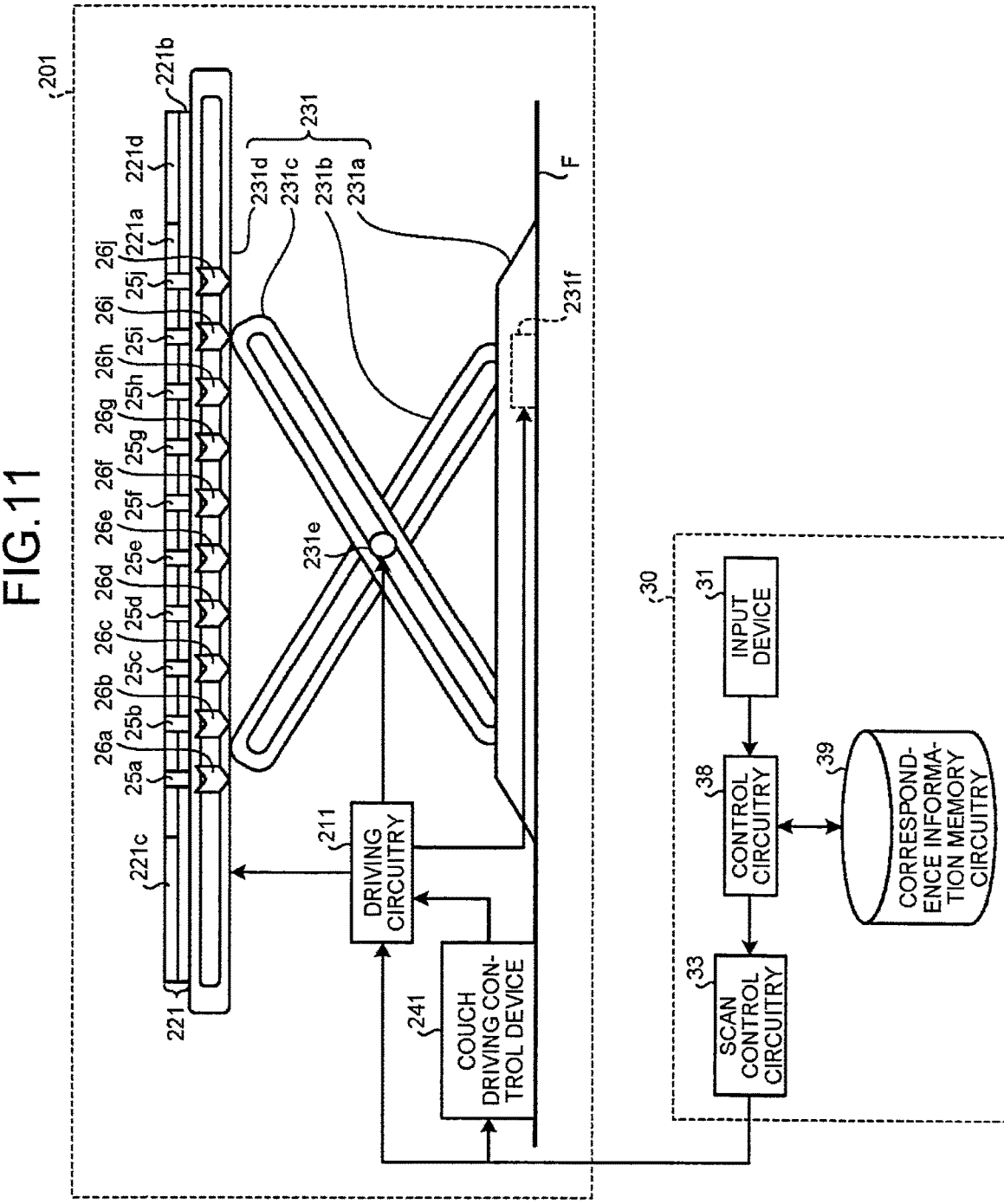
FIG. 11 is a configuration example of a couch device according to a third embodiment.

In a third embodiment, a situation when a transformable couchtop is transformed by the configuration different from the couch device 20 explained in the first embodiment and the second embodiment, is described with reference to FIG. 11 and the like. FIG. 11 is a configuration example of a couch device according to the third embodiment.

A couch device 201 according to the third embodiment illustrated in FIG. 11 is installed instead of the couch device 20 in the X-ray CT apparatus according to the first embodiment illustrated FIG. 1. An X-ray CT apparatus according to the third embodiment is configured the same as the X-ray CT apparatus according to the first embodiment illustrated in FIG. 1, except that the couch device 201 is installed instead of the couch device 20, and correspondence information memory circuitry 39 illustrated in FIG. 11 is newly installed in the console device 30. For example, the gantry device 10 is configured so as to be inclinable relative to the floor surface F, similar to that in the second embodiment.

The couch device 201 according to the third embodiment, as illustrated in FIG. 11, includes a couchtop 221, shape control members 26a to 26j, and driving circuitry 211. The couchtop 221 is a plate on which the subject P is to be laid. The driving circuitry 211 moves the couchtop 221 to the opening of the gantry device 10 that collects data (data on detected X-rays) used for taking a medical image, based on an instruction from the control circuitry 38 under the control of the scan control circuitry 33. The couch device 201 includes a couch driving control device 241 for controlling the driving circuitry 211, in addition to the scan control circuitry 33. The operator can drive and control the entire couch device 201, by operating the couch driving control device 241. The couch driving control device 241 can also control the entire couch device 201, in conjunction with the scan control circuitry 33 and the control circuitry 38.

As illustrated in FIG. 11, the couchtop 221 includes a movable base couchtop 221b and a transformable couchtop 221a. The movable base couchtop 221b is a couchtop that transfers the transformable couchtop 221a to the opening of the gantry device 10. The transformable couchtop 221a is mounted above the movable base couchtop 221b. The transformable couchtop 221a is configured so as to be capable of bending a part thereof from a flat shape. The shape control members 26a to 26j control the shape of the transformable couchtop 221a.

The couch device 201 according to the third embodiment, as illustrated in FIG. 11, also includes a movable couchtop fixing member 221c arranged at one end of the couchtop 221 in the longitudinal direction and an immovable couchtop fixing member 221d arranged at the other end of the couchtop 221 in the longitudinal direction, as couchtop fixing members that adjust the transformation degree of the transformable couchtop 221a. In the example illustrated in FIG. 11, the immovable couchtop fixing member 221d is arranged at the right-hand side of the couchtop 221 that is first inserted into the opening. The movable couchtop fixing member 221c is arranged at the left-hand side of the couchtop 221 that has a possibility of not inserted into the opening.

The shape control members 26a to 26j control the movable couchtop fixing member 221c to move in the longitudinal direction of the couchtop 221, so as to transform the transformable couchtop 221a into a certain shape. For example, as described in the second embodiment, the driving circuitry 211 moves the transformable couchtop 221a to the opening, while a part thereof is bent.

As illustrated in FIG. 11, a support member 231 supports the couchtop 221. The support member 231 supports the couchtop 221 so as to be movable in the vertical direction and inclinable. Hereinafter, an elevation mechanism and an inclination mechanism of the support member 231 performed in the third embodiment are explained first, followed by an explanation on a couchtop transformation mechanism performed in the third embodiment.

The support member 231, as illustrated in FIG. 11, includes a base 231a installed on the floor surface F and an elevator 231f. The support member 231 includes a support plate 231d on which the couchtop 221 is mounted. In the example illustrated in FIG. 11, the shape control members 26a to 26j, which will be described in detail below, are arranged at the support plate 231d. In the example illustrated in FIG. 11, the elevator 231f is built inside the base 231a.

The support member 231, as illustrated in FIG. 11, includes a pair of link arms including an outer arm 231c and an inner arm 231b that are linked in an X-shape. The link arms are provided between the base 231a and the couchtop 221 and face each other with a space therebetween in the width direction (short side direction) of the couchtop 221. In the example illustrated in FIG. 11, the link arms are provided between the base 231a and the support plate 231d.

The elevator 231f moves the couchtop 221 in the vertical direction, by raising and lowering the pair of link arms including the outer arm 231c and the inner arm 231b linked in an X-shape. For example, the end of the upper side of the outer arm 231c and the end of the upper side of the inner arm 231b are fixed to the support plate 231d, and the end of the lower side of the outer arm 231c is fixed to the base 231a. The end of the lower side of the inner arm 231b is slidably installed on the base 231a along the longitudinal direction. The elevator 231f slides the end of the lower side of the inner arm 231b in the longitudinal direction, while a fulcrum 231e of the linking portion of the outer arm 231c and the inner arm 231b is being fixed. Accordingly, the couchtop 221 mounted on the support plate 231d is moved in the vertical direction. In the example illustrated in FIG. 11, the elevator 231f moves the couchtop 221 in the vertical direction by an instruction from the driving circuitry 211.

Figure 12:
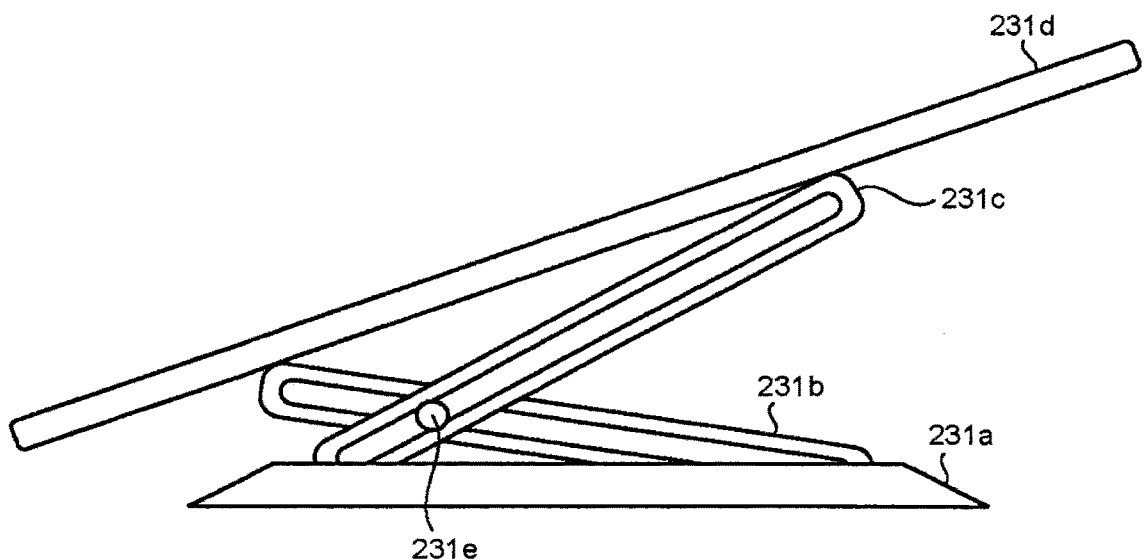
FIG. 12 is a schematic diagram for explaining an inclination mechanism of the couch device according to the third embodiment.

In the third embodiment, the fulcrum 231e of the linking portion of the outer arm 231c and the inner arm 231b is movably configured, so as to support the couchtop 221 to be inclinable. The couchtop 221 is inclined in the longitudinal direction with the movement of the fulcrum 231e. FIG. 12 is a schematic diagram for explaining an inclination mechanism of the couch device according to the third embodiment. In FIG. 12, when the movable fulcrum 231e moves in the left direction, the support plate 231d is inclined counterclockwise. Subsequently, the couchtop 221 mounted on the support plate 231d is also inclined counterclockwise. In the examples illustrated in FIG. 11 and FIG. 12, the driving circuitry 211 moves the fulcrum 231e. However, in the third embodiment, fulcrum driving circuitry for moving the fulcrum 231e may be separately provided.

Figure 13:
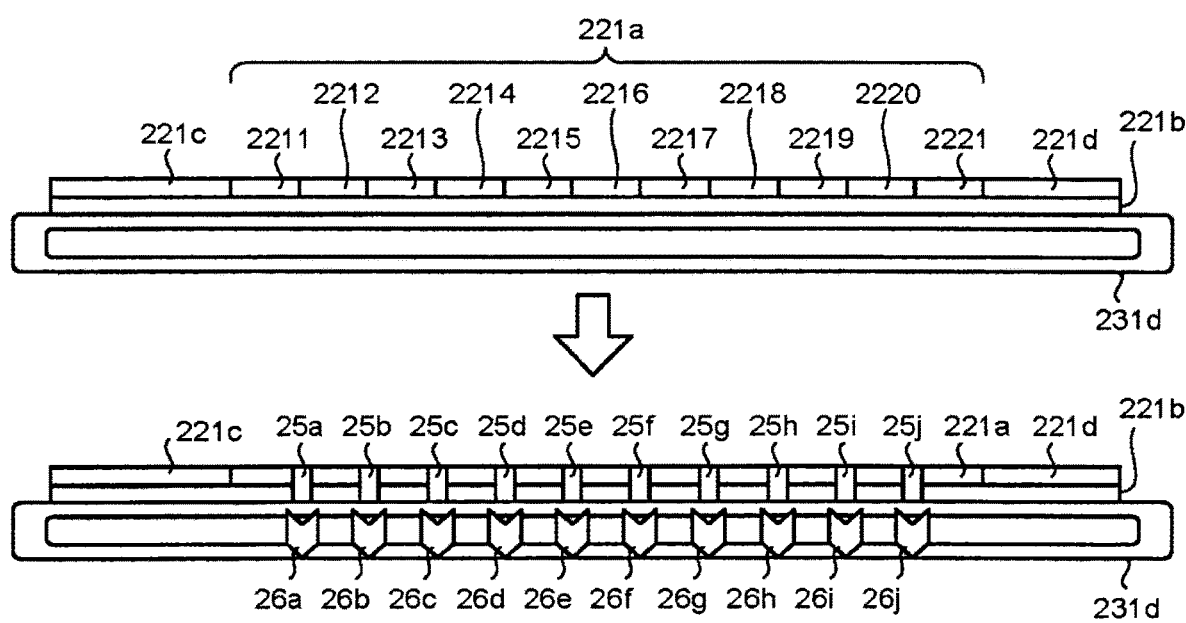
FIG. 13, FIG. 14 and FIG. 15 are schema c diagrams for explaining a couchtop transformation mechanism of the couch device according to the third embodiment.
Figure 14:
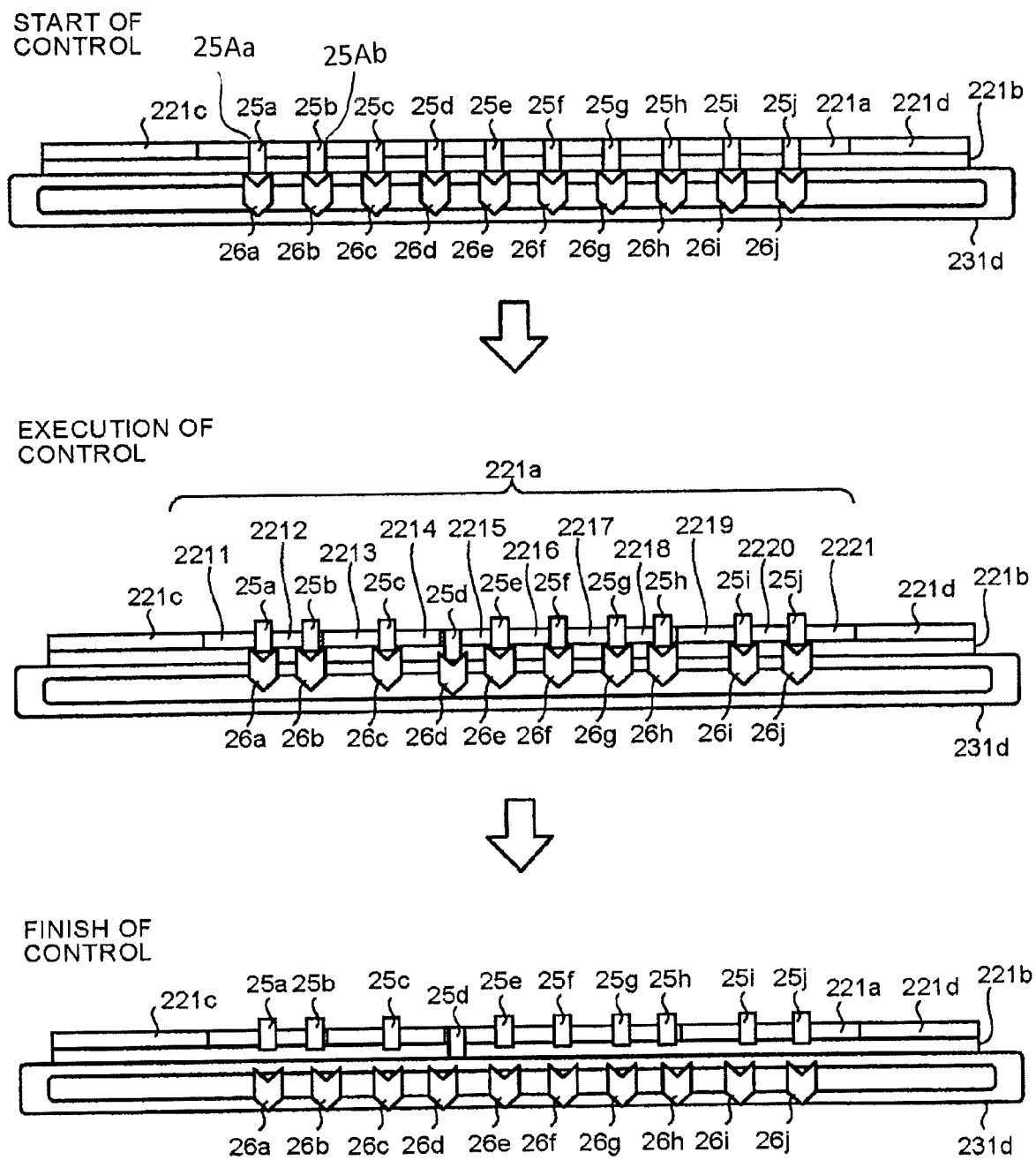
Figure 15:
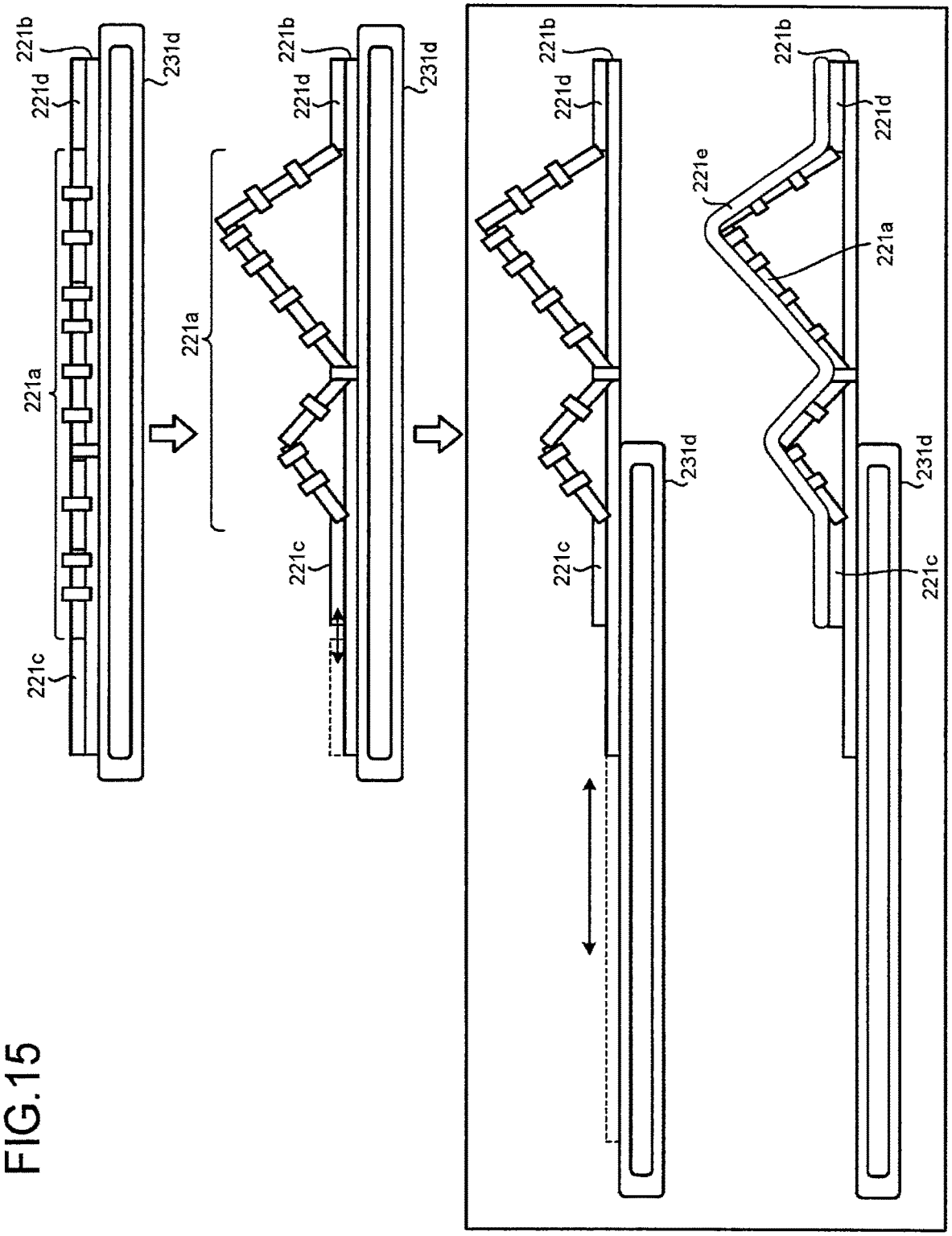

The couchtop transformation mechanism according to the third embodiment will now be described with reference to FIGS. 13 to 15, in addition to FIG. 11. FIGS. 13 to 15 are schematic diagrams for explaining the couchtop transformation mechanism of the couch device according to the third embodiment.

The transformable couchtop 221a includes a plurality of divided couchtops, which are divided at predetermined intervals. In the upper example illustrated in FIG. 13, the transformable couchtop 221a includes 11 pieces of divided couchtops 2211 to 2221. The divided couchtops 2211 to 2221 have the same size. For example, the divided couchtops 2211 to 2221 are connected with each other in a bendable manner by hinges. Such hinges, for example, are made of the same material as that of the divided couchtops 2211 to 2221.

As illustrated in FIG. 11 and the lower diagram in FIG. 13, transformation support members 25a to 25j that fix the transformable couchtop 221a to the movable base couchtop 221b are fitted to the respective divided sections of the transformable couchtop 221a. As illustrated in FIG. 11 and the lower diagram in FIG. 13, ten pieces of the shape control members 26a to 26j are provided for ten pieces of the transformation support members 25a to 25j, respectively. For example, the transformation support members 25a to 25j are made of the same material as that of the divided couchtops 2211 to 2221, and can be fixed to the transformable couchtop 221a with latches. The transformation support members 25a to 25j can also be fixed to the movable base couchtop 221b with latches.

The shape control members 26a to 26j adjust the position of a specific transformation support member among the multiple transformation support members 25a to 25j so that the installation location of the specific transformation support member is a fixed point relative to the movable base couchtop 221b. Hereinafter, the fixed point may be referred to as a "couchtop fixing portion".

The transformation support members 25a to 25j each, while not being fixed to the movable base couchtop 221b, by being fixed to the position apart from the divided section to be fitted, allow a divided couchtop adjacent to the divided section to be bendable. The transfomiation support members 25a to 25j each, while not being fixed to the movable base couchtop 221b, by being fixed to the divided section to be fitted, allow a divided couchtop adjacent to the divided section to be unbendable.

At the portion where the transformable couchtop 221a is separated from the movable base couchtop 221b and is extended, the shape control members 26a to 26j adjust the installation location of the transformation support member placed on the portion so that it becomes "unbendable" as described above. Hereinafter, this portion may be referred to as a "free fixing portion".

At a portion where the transformable couchtop 221a is separated from the movable base couchtop 221b and is bent, the shape control members 26a to 26j adjust the installation location of the transformation support member placed on the portion so that it becomes "bendable" as described above. Hereinafter, this portion may be referred to as a "bending portion".

Hereinafter, an example of controlling the shape of couchtop will be described. The following example is executed after determining the positions of the "couchtop fixing portion", the "free fixing portion", and the "bending portion" of the transformable couchtop 221a, and the moving distance of the movable couchtop fixing member 221c by setting the shape of couchtop.

At the "start of control" illustrated in FIG. 14, the shape of the transformable couchtop 221a is in a flat shape, which is an initial shape, by the control of the control circuitry 38. The transformation support members 25a to 25j are moved to the positions of the divided sections (hinges) 25Aa, 25Ab, etc., respectively. The shape control members 26a to 26j are moved directly below the transformation support members 25a to 25j, respectively. The positions of the transformation support members 25a to 25j are adjusted by the shape control members 26a to 26j, and the positions of the shape control members 26a to 26j are adjusted by the driving circuitry 211.

At the "execution of control" illustrated in FIG. 14, the shape control members 26a to 26j hold the transformation support members 25a to 25j, respectively, and adjust the positions of the transformation support members 25a to 25j, respectively. For example, the transformation support member 25d is fixed to the movable base couchtop 221b, by being moved by the shape control member 26d from the position between the divided couchtop 2214 and the divided couchtop 2215, to the position left of the divided couchtop 2215 to the right, and further downward to the joint portion of the movable base couchtop 221b. As a result, the "couchtop fixing portion" is formed.

The transformation support member 25b is fixed to the transformable couchtop 221a, by being moved by the shape control member 26b from the position between the divided couchtop 2212 and the divided couchtop 2213, to the position right of the divided couchtop 2212 in the left direction. Accordingly, the portion between the divided couchtop 2212 and the divided couchtop 2213 becomes bendable by a hinge, while being separated from the movable base couchtop 221b. The transformation support member 25h is fixed to the transformable couchtop 221a, by being moved by the shape control member 26h from the position between the divided couchtop 2218 and the divided couchtop 2219, to the position right of the divided couchtop 2218 in the left direction. Accordingly, the portion between the divided couchtop 2218 and the divided couchtop 2219 becomes bendable by a hinge, while being separated from the movable base couchtop 221b.

Extending the divided couchtop 2211 and the divided couchtop 2212 with the couchtops separated from the movable couchtop base 221b allows the shape control member 26a to fix the transformation support member 25a to the transformable couchtop 221a at the position between the divided couchtop 2211 and the divided couchtop 2212. Accordingly, the hinge that connects the divided couchtop 2211 and the divided couchtop 2212 becomes unbendable, and the "free fixing portion" is formed. The positions of the transformation support members 25c, 25e, 25f, 25g, and 25i are similarly adjusted by the shape control members 26c, 26e, 26f, 26g, and 26i, as described above. Hence, the divided couchtops 2213 and 2214 become unbendable, the divided couchtops 2215, 2216, and 2218 become unbendable, and the divided couchtops 2219, 2220, and 2221 become unbendable.

At the "finish of control" illustrated in FIG. 14, the shape control members 26a to 26j separate from the transformation support members 25a to 25j, respectively, and return to the initial positions.

As illustrated in the first and second stages in FIG. 15, the movable couchtop fixing member 221c moves to the right along the longitudinal direction. Fixing the immovable couchtop fixing member 221d to the movable base couchtop 221b so as not to move allows the transformable couchtop 221a to be transformed into the shape of a chair from a flat shape, from the respective fixed positions of the transformation support members 25a to 25j. Although not illustrated, a shape control member for the movable couchtop fixing member 221c is installed immediately below the movable couchtop fixing member 221c. The movable couchtop fixing member 221c is moved by adjusting the position of this shape control member. The driving circuitry 211 may also move the movable couchtop fixing member 221c.

As illustrated in the upper diagram of the third stage in FIG. 15, the driving circuitry 211 moves the movable base couchtop 221b towards the opening at the time of imaging. In practice, as illustrated in the upper diagram of the third stage in FIG. 15, a mattress 221e is placed above the transformable couchtop 221a, which is transformed into the shape of a chair, and the subject P sits on the mattress 221e.

The couch device 201 according to the third embodiment can transform the transformable couchtop 221a into any desired shape, by the mechanisms of the transformation support members 25a to 25j and the shape control members 26a to 26j. Accordingly, in the third embodiment, it is also possible to obtain the effects similar to those described in the first embodiment and those described in the second embodiment.

The movable couchtop fixing member 221c is preferably manufactured of hard metal and the like because it moves the transformable couchtop 221a. However, if metal is placed within an area of the imaging range, metal artifacts are produced in X-ray CT image data. Consequently, it is preferable to arrange the movable couchtop fixing member 221c illustrated in FIG. 11 and the like at the left-hand side of the couchtop 221 so that the movable couchtop fixing member 221c is arranged in an area outside the imaging range. On the other hand, the immovable couchtop fixing member 221d arranged at the right-hand side of the couchtop 221 is placed within an area of the imaging range during imaging. Accordingly, it is preferably configured as a latch made of resin, carbon, or the like.

Figures 16, 17:
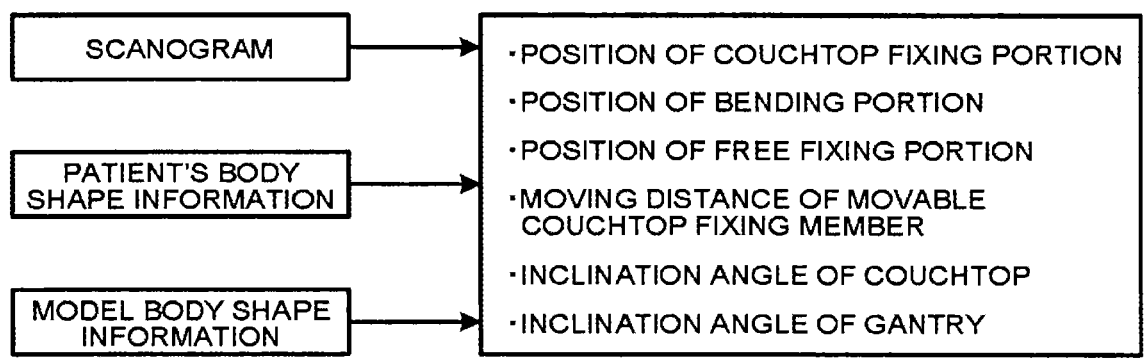
FIG. 16 and FIG. 17 are schematic diagrams for explaining processing of control circuitry according to the third embodiment.

A setting method of the shape of couchtop performed by the control circuitry 38 according to the third embodiment will now be described with reference to FIG. 16, FIG. 17, and the like. FIG. 16 and FIG. 17 are schematic diagrams for explaining processing of control circuitry according to the third embodiment. Either the couch driving control device 241 or the gantry device 10 may carry out the contents described below. Moreover, the contents described below are also applicable to the first embodiment and the second embodiment.

The control circuitry 38 according to the third embodiment acquires information related to imaging of the subject P, and sets the shape of the transformable couchtop 221a on Which the subject P is to be laid, based on the acquired information. The control circuitry 38 then controls the couchtop 221 so that the transformable couchtop 221a is transformed into a preset shape. The control circuitry 38 controls the couchtop 221 via the driving circuitry 211.

Conceptually, as described in the second embodiment, the control circuitry 38 sets the shape of the transformable couchtop 221a so that the posture of the subject P is in a posture suitable for imaging, based on the information related to imaging of the subject P. For example, the control circuitry 38 sets the shape of the transformable couchtop 221a so that the imaging time of the subject P is reduced. Alternatively, for example, the control circuitry 38 sets the shape of the transformable couchtop 221a so that it does not come into contact with the opening. Alternatively, for example, the control circuitry 38 sets the shape of the transformable couchtop 221a so that the subject P can take the posture. As described in the second embodiment, the control circuitry 38 not only sets the shape of the transformable couchtop 221a, but also inclines at least one of the support member 231 or the gantry device 10 so that the posture of the subject P is in a posture suitable for imaging.

The setting method of the shape of couchtop performed by the control circuitry 38 is roughly classified into three setting methods described below. As illustrated in FIG. 11, the control circuitry 38 is connected to the correspondence information memory circuitry 39. In the first setting method, the control circuitry 38 uses the correspondence information memory circuitry 39. The correspondence information memory circuitry 39 stores therein correspondence information corresponding to the shape of transformable couchtop 221a for each imaging plan. The control circuitry 38 then obtains the shape corresponding to the "imaging plan for the subject P" acquired as the "information related to imaging of the subject P", from the correspondence information memory circuitry 39.

For example, as illustrated in FIG. 16, the correspondence information memory circuitry 39 stores therein correspondence information in which the "shape: sitting position" is associated with the "imaging plan: swallowing movements", and the "shape: sitting position" is associated with the "imaging plan: inspiration and expiration movements". The pieces of correspondence information such as these, as described in the second embodiment, are stored in the correspondence information memory circuitry 39, because the dynamic imaging of swallowing and the dynamic imaging of inspiration and expiration are preferably performed while the subject P whose image is to be taken is in the upright position.

For example, as illustrated in FIG. 16, the correspondence information memory circuitry 39 stores therein correspondence information in which the "shape: sitting position" is associated with the "imaging plan: volume", As described in the second embodiment, this correspondence information is stored in the correspondence information memory circuitry 39 as a result of transformation of the transformable couchtop 221a into the shape of a chair, which increases the reconstruction region and thus causes the volume imaging to be executable by conventional scan that can reduce imaging time.

For example, the operator inputs the "swallowing movements" or the "information indicating that dynamic imaging of swallowing is to be performed" as an imaging plan by using the input device 31. In such a case, the control circuitry 38 obtains the "shape: sitting position" associated with the "swallowing movements" by referring to the correspondence information memory circuitry 39, and notifies the "shape: sitting position" to the driving circuitry 211. Alternatively, the operator inputs the "volume imaging" or the "conventional scan" as an imaging plan by using the input device 31. In such a case, the control circuitry 38 obtains the "shape: sitting position" associated with the "volume" by referring to the correspondence information memory circuitry 39, and notifies the "shape: sitting position" to the driving circuitry 211. As a result, the couchtop transformation control illustrated in FIG. 14 and FIG. 15 is performed.

In the first setting method described above, for example, the control circuitry 38 uses initially set values for the positions of the "couchtop fixing portion", the "free fixing portion" and the "bending portion" of the transformable couchtop 221a, and the moving distance of the movable couchtop fixing member 221c. Alternatively, for example, the control circuitry 38 calculates the positions of the "couchtop fixing portion", the "free fixing portion" and the "bending portion" of the transformable couchtop 221a, and the moving distance of the movable couchtop fixing member 221c, by using model body shape information corresponding to age, sex, height, weight, and the like of the subject P. A plurality of pieces of model body shape information corresponding to various body shapes may be stored in the control circuitry 38 or stored in the correspondence information memory circuitry 39. The correspondence information memory circuitry 39 is not limited to be built in the console device 30 and the like in the X-ray CT apparatus, but for example, may be installed in a hospital network communicable with the control circuitry 38.

The second setting method will now be described. In the second setting, the control circuitry 38 sets the shape of the transformable couchtop 221a, based on the "physical information on the subject P" acquired as the "information related to imaging of the subject 2". The "physical information on the subject P", for example, as illustrated in FIG. 17, is a scanogram taken as a positioning image. Alternatively, the "physical information on the subject P", for example, as illustrated in FIG. 17, is the "patient's body shape information" including the detailed physical measurement results of the subject P. Alternatively, the "physical information on the subject P", for example, as illustrated in FIG. 17, is model body shape information corresponding to age, sex, height, weight, and the like of the subject P.

The control circuitry 38 can calculate the positions of the head, the waist, and the knees of the subject P laid on the flat transformable couchtop 221a by using the "physical information on the subject P". Accordingly, the control circuitry 38, for example, can calculate various parameters related to the shape of the transformable couchtop 221a so that the subject P can comfortably sit thereon. The control circuitry 38 can also calculate the shape of the transformable couchtop 221a the inclination angle of the couchtop 221, and the inclination angle of the gantry device 10 no that the subject P will not come into contact with the opening, from the geometry of the X-ray CT apparatus stored in advance.

For example, the control circuitry 38 calculates various parameters based on the scanogram of the subject P so that the shape of the transformable couchtop 221a enables volume imaging of an internal organ to be imaged set in the imaging plan and that the subject P will not come into contact with the opening. The various parameters, as illustrated in FIG. 17, include the position of couchtop fixing portion, the position of bending portion, the position of free fixing portion, and the moving distance of movable couchtop fixing member. The control circuitry 38, as illustrated in FIG. 17, may also calculate the inclination angle of couchtop and the inclination angle of gantry as various parameters, according to the need.

The "physical information on the subject P" may be information such as the posture that can be taken by the subject P is the "sitting position". In such a case, the control circuitry 38 calculates various parameters related to the shape of the transformable couchtop 221a so that the transformable couchtop 221a is in a chair shape in which the subject P will not come into contact with the opening. The "physical information on the subject P" may also be information such as the "subject P has difficulty in bending the knees and is difficult to keep a lying position". In such a case, the control circuitry 38 calculates various parameters related to the shape of the transformable couchtop 221a so that the transformable couchtop 221a is in a legless chair shape that enables the subject P to sit without bending his/her knees as well as in the shape in which the subject P will not come into contact with the opening.

The third setting method will now be described. The third setting method is a method that combined the first setting method and the second setting method. In the third setting method, the control circuitry 38 obtains the shape corresponding to the imaging plan of the subject P acquired as information related to imaging of the subject P, from the correspondence information memory circuitry 39. The control circuitry 38 then adjusts the shape obtained from the correspondence information memory circuitry 39 based on the physical information on the subject P acquired as information related to imaging of the subject P. The control circuitry 38 then controls the transformable couchtop 221*a* so that it is transformed into the adjusted shape.

For example, even if the control circuitry 38 obtains the "shape: sitting position" from the "imaging plan: swallowing movements", when it obtains information such as the "subject P has difficulty in bending the knees" as the "physical information on the subject P", the control circuitry 38 adjusts the various parameters so that the shape of the transformable couchtop 221*a* is in a "legless chair". Alternatively, even if the control circuitry 38 obtains the "shape: sitting position" from the "imaging plan: volume", when it cannot obtain the shape and the inclination angle capable of avoiding the subject P from coming into contact with the opening, from the "physical information on the subject P", the control circuitry 38 sets the shape of the transformable couchtop 221*a* into "flat".

In this manner, in the third embodiment, it is possible to set the shape of the transformable couchtop 221*a* so that the posture of the subject P is in a posture suitable for imaging, based on the information related to imaging of the subject P.

A medical image diagnostic apparatus in which the couch device 20 described in the first embodiment and the second embodiment and a medical image diagnostic apparatus in which the couch device 201 described in the third embodiment is installed are not limited to the X-ray CT apparatus. The couch device 20 or the couch device 201 can be installed in any of the medical image diagnostic apparatuses that include an opening into which the subject P is to be inserted and a gantry device for collecting data used for taking medical images.

Such a medical image diagnostic apparatus, for example, includes a magnetic resonance imaging (MRI) apparatus, and a nuclear medical imaging apparatus such as a single photon emission computed tomography (SPECT) apparatus or a positron emission computed tomography (PET) apparatus. Such a medical image diagnostic apparatus, for example, includes a PET-CT apparatus, a SPECT-CT apparatus, a PET-MRI apparatus, and a SPECT-MRI apparatus.

The constituents of each of the apparatuses illustrated in the first embodiment to the third embodiment are functionally conceptual, and are not necessarily required to be physically configured as illustrated. In other words, the specific mode of dispersion and integration of each apparatus is not limited to the ones illustrated in the drawings, and all or a part thereof can be functionally or physically dispersed or integrated in an optional unit, depending on various kinds of load and the status of use. All or an optional part of the respective processing functions carried out in each apparatus are realized by a CPU and a computer program analyzed and executed by the CPU, or may be realized as hardware by the wired logic.

As described above, according to the first embodiment to the third embodiment, it is possible to reduce the preparation time for imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modified examples as would fall within the scope and spirit of the inventions.

What is claimed is:

1. A couch device, comprising:
a couchtop that includes a movable base couchtop and a transformable couchtop mounted above the movable base couchtop and capable of bending a part thereof from a flat shape;
shape control members configured to control a shape of the transformable couchtop; and
driving circuitry configured to move the couchtop to an opening of a gantry device that collects data used for taking a medical image; wherein
the transformable couchtop comprises a plurality of divided couchtops divided at a predetermined interval and a plurality of divided sections; the couchtop comprises a plurality of transformation support members to fix the transformable couchtop onto the movable base couchtop for each of the plurality of divided sections; and
each of the shape control members adjusts a position of a specific transformation support member among the plurality of transformation support members so that an installation location of the specific transformation support member is a fixed point relative to the movable base couchtop.

2. The couch device according to claim 1, wherein
each of the plurality of transformation support members, in a state not being fixed to the movable base couchtop, by being fixed to a position apart from a respective divided section of the plurality of divided sections to be fitted, allows one of the plurality of divided couchtops adjacent to the respective divided section to be in a bendable state, and by being fixed to the respective divided section to be fitted, allows the one of the plurality of divided couchtops adjacent to the respective divided section to be in an unbendable state, and each of the shape control members, at a portion where the transformable couchtop separates from the movable base couchtop and is extended, adjusts the installation location of the transformation support member placed on the portion to be in the unbendable state, and at the portion where the transformable couchtop separates therefrom and is bent, adjusts the installation location of the transformation support member placed on the portion to be in the bendable state.

3. The couch device according to claim 1, wherein the driving circuitry is configured to move the transformable couchtop to the opening of the gantry device while a part thereof is bent.

4. The couch device according to claim 1, further comprising a couchtop fixing member configured to adjust a transformation degree of the transformable couchtop.

5. The couch device according to claim 4, wherein
the couchtop fixing member includes a movable couchtop fixing member arranged at one end of the couchtop in a longitudinal direction and an immovable couchtop fixing member arranged at another end, and
each of the shape control members is configured to control the movable couchtop fixing member so that the movable couchtop fixing member moves in a longitudinal direction of the couchtop to transform the transformable couchtop into a certain shape.

6. The couch device according to claim 5, wherein the movable couchtop fixing member is arranged in an area outside an imaging range.

7. The couch device according to claim 1, further comprising a support member that supports the couchtop to be movable in a vertical direction and inclinable.

8. The couch device according to claim 7, wherein the support member includes:
   a base to be installed on a floor surface,
   a pair of link arms including an outer arm and an inner arm that are linked in an X-shape and provided between the base and the couchtop so as to face each other with a space therebetween in a width direction of the couchtop;
   a linking portion linking the pair of link arms;
   an elevator that moves the couchtop in a vertical direction by raising and lowering the pair of link arms, wherein
   a fulcrum of the linking portion of the outer arm and the inner arm in the link arms is movable, and
   the couchtop is inclined in a longitudinal direction by a movement of the fulcrum.

9. An X-ray computed tomography (CT) device, comprising:
   a couch device that includes a couchtop that includes a movable base couchtop and a transformable couchtop mounted above the movable base couchtop and capable of bending a part thereof from a flat shape, the transformable couchtop comprising a plurality of divided couchtops that are inseparable;
   a gantry device that includes a portion defining an opening into which a subject is to be inserted and configured to collect data on detected X-ray; and
   control circuitry configured to control the couchtop by acquiring information related to imaging of the subject, setting a shape of the transformable couchtop on which the subject is to be laid based on the acquired information, and transforming the transformable couchtop into the set shape.

10. The X-ray CT apparatus according to claim 9, further comprising memory circuitry, connected to the control circuitry, that correspondingly stores the shape of the transformable couchtop for each imaging plan, and obtains a shape corresponding to an imaging plan of the subject acquired as the information from the memory circuitry.

11. The X-ray CT apparatus according to claim 9, wherein the control circuitry sets the shape of the transformable couchtop, based on physical information on the subject acquired as the information.

12. The X-ray CT apparatus according to claim 9, further comprising memory circuitry, connected to the control circuitry, that correspondingly stores the shape of the transformable couchtop for each imaging plan, obtains a shape corresponding to an imaging plan of the subject acquired as the information from the memory circuitry, adjusts the shape obtained from the memory circuitry based on physical information on the subject acquired as the information, and controls the transformable couchtop to transform into an adjusted shape.

13. The X-ray CT apparatus according to claim 9, wherein the control circuitry sets the shape of the transformable couchtop so that a posture of the subject is in a posture suitable for imaging.

14. The X-ray CT apparatus according to claim 13, wherein the control circuitry sets the shape of the transformable couchtop so that an imaging time of the subject is reduced.

15. The X-ray CT apparatus according to claim 13, wherein the control circuitry sets the shape of the transformable couchtop so that the subject does not come into contact with the opening.

16. The X-ray CT apparatus according to claim 13, wherein the control circuitry sets the shape of the transformable couchtop so that the subject can take a posture.

17. The X-ray CT apparatus according to claim 13, wherein
   the couch device further includes a support member that supports the couchtop to be movable in a vertical direction and inclinable,
   the gantry device is inclinable relative to a floor surface, and
   the control circuitry sets the shape of the transformable couchtop and inclines at least one of the support member or the gantry device so that the posture of the subject is suitable for imaging.

* * * * *